US011611705B1

(12) United States Patent
Chen

(10) Patent No.: US 11,611,705 B1
(45) Date of Patent: Mar. 21, 2023

(54) SMART GLASSES WITH AUGMENTED REALITY CAPABILITY FOR DENTISTRY

(71) Applicant: Julian W. Chen, Santa Monica, CA (US)

(72) Inventor: Julian W. Chen, Santa Monica, CA (US)

(*) Notice: Subject to any disclaimer, the term of this patent is extended or adjusted under 35 U.S.C. 154(b) by 292 days.

(21) Appl. No.: 16/893,109

(22) Filed: Jun. 4, 2020

Related U.S. Application Data

(60) Provisional application No. 62/859,285, filed on Jun. 10, 2019.

(51) Int. Cl.
| | | |
|---|---|---|
| *H04N 5/232* | (2006.01) | |
| *G06F 3/01* | (2006.01) | |
| *G16H 10/60* | (2018.01) | |
| *G06T 11/00* | (2006.01) | |
| *G06V 40/16* | (2022.01) | |
| *H04N 7/18* | (2006.01) | |

(52) U.S. Cl.
CPC ......... *H04N 5/23296* (2013.01); *G06F 3/011* (2013.01); *G06T 11/00* (2013.01); *G06V 40/172* (2022.01); *G16H 10/60* (2018.01); *H04N 5/23203* (2013.01); *H04N 5/23219* (2013.01); *H04N 7/183* (2013.01)

(58) Field of Classification Search
CPC ............ H04N 5/2329; H04N 5/23219; H04N 5/232036; H04N 7/183; H04N 13/332; G06F 3/011; G06T 11/00; G06V 40/172; G16H 10/60
See application file for complete search history.

(56) References Cited

U.S. PATENT DOCUMENTS

| | | | | |
|---|---|---|---|---|
| 6,847,336 B1* | 1/2005 | Lemelson | .............. | H04N 7/147 345/8 |
| 2001/0021108 A1* | 9/2001 | Shimada | ................ | A61B 90/30 362/276 |
| 2010/0259619 A1* | 10/2010 | Nicholson | ........ | H04N 5/225251 348/158 |
| 2016/0025978 A1* | 1/2016 | Mallinson | .......... | G02B 27/0172 345/8 |
| 2016/0188277 A1* | 6/2016 | Miyasaka | ............. | G06F 3/1454 345/2.2 |
| 2018/0168780 A1* | 6/2018 | Kopelman | ............. | A61B 34/10 |

* cited by examiner

*Primary Examiner* — Nelson D. Hernández Hernández
(74) *Attorney, Agent, or Firm* — Patent Law Works LLP

(57) ABSTRACT

The present disclosure describes smart glasses that support variable magnification of an operating field and hands-free operations in dentistry. One or more operations and functions efficiently achieved via the smart glasses comprise: receiving, with smart glasses, a user-initiated request for a specific operation; activating, using the smart glasses, a camera with initial settings; generating a floating image through a micro-projector and a specifically-coated prism coupled to the camera; receiving a user input to adjust a camera setting to adjust the floating image; and dynamically controlling, using the smart glasses, the camera for the specific operation.

17 Claims, 25 Drawing Sheets

SMART GLASSES WITH AUGMENTED REALITY CAPABILITY FOR DENTISTRY

CROSS-REFERENCES TO RELATED APPLICATIONS

This application claims the benefit of U.S. Provisional Patent Application No. 62/859,285, entitled "Smart Glasses with Augmented Reality Capability for Dentistry" filed Jun. 10, 2019, the entire content of which is herein incorporated by reference.

FIELD OF THE INVENTION

The present disclosure relates to tools to improve dental operations. In particular, the present disclosure relates to smart glasses that support variable magnification of the operating field of view and hands-free operations in dentistry.

BACKGROUND OF THE DISCLOSURE

Most current augmented reality (AR) devices are designed for gaming and entertainment. Some AR devices or glasses have been utilized for commercial applications, but they are used to superimpose a virtual image over the surrounding environment. There are not AR devices or glasses that are designed to take advantage of the advanced digital camera technology available today to supplant traditional optical surgical glasses and loupes.

Currently in the market, dental and medical surgical loupes utilize a traditional frame and/or goggle design. When magnification is needed, optical elements are affixed onto the lenses of glasses or into plastic goggle lens, which requires a trained technician to measure the inter-pupillary distance of each user (e.g., a dentist, a surgeon), drill holes into the lenses or goggles based on this distance, and mount the optical elements to the proper distance. This prevents mass production, and thus significantly increases time and cost to manufacture.

Moreover, because magnifying optical elements are made of glasses, the existing surgical loupes are extremely heavy and bulky. When a user chooses optical elements with greater magnification or variable-zoom, the surgical loupes are even more bulky and heavy.

It is therefore desirable to find a way to not only accommodate various surgical conditions/requirements with varying degrees of magnification but also significantly reduce the weight and bulk of the existing glasses and loupes to improve the user experience.

SUMMARY

The techniques introduced herein overcome the deficiencies and limitations of the prior art at least in part by providing smart glasses that support variable magnification of operating field and hands-free operations in dentistry.

According to one innovative aspect of the subject matter described in this disclosure, a method for enabling variable adjustments of the operating field of view and hands-free operations in dentistry is provided. The method includes receiving, with smart glasses, a user-initiated request for a specific operation; activating, using the smart glasses, a camera with initial settings; generating a floating image through a micro-projector and a specifically-coated prism coupled to the camera; receiving a user input to adjust a camera setting to adjust the floating image; and dynamically controlling, using the smart glasses, the camera for the specific operation.

According to another innovative aspect of the subject matter described in this disclosure, a pair of smart glasses for enabling variable adjustments of the operating field of view and hands-free operations in dentistry is provided. The smart glasses include a camera for capturing one or more images and videos; and a control unit configured to: receive a user-initiated request for a specific operation; activate the camera with initial settings; generate floating image through a micro-projector and a specifically-coated prism coupled to the camera; receive a user input to adjust a camera setting to adjust the floating image; and dynamically control the camera for the specific operation.

Other implementations of one or more of these aspects and other aspects include corresponding systems, apparatus, and computer programs, configured to perform the various action and/or store various data described in association with these aspects. Numerous additional features may be included in these and various other implementations, as discussed throughout this disclosure It should be understood that the language used in the present disclosure has been principally selected for readability and instructional purposes, and not to limit the scope of the subject matter disclosed herein.

BRIEF DESCRIPTION OF THE DRAWINGS

The present disclosure is illustrated by way of example, and not by way of limitation in the figures of the accompanying drawings in which like reference numerals are used to refer to similar elements.

DETAILED DESCRIPTION

Figure 1A:
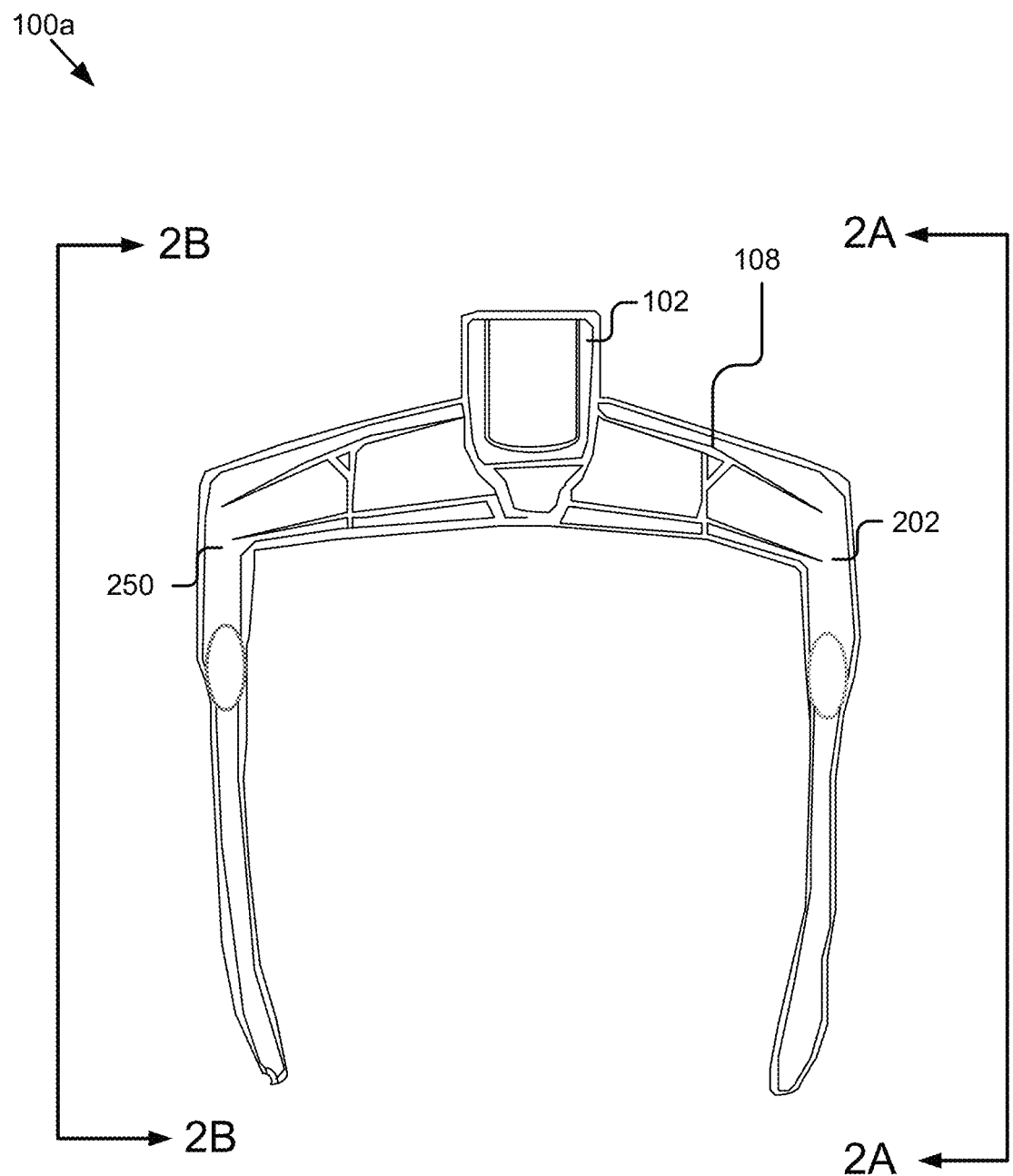
FIG. 1A is a top plan view of a first implementation of smart glasses with a single camera in accordance with the present disclosure.

As set forth in detail below, the technology described herein provides smart glasses 100 (also referred to in this application as smart augmented reality (AR) goggles, AR glasses, or smart AR glasses, etc.) used in dentistry. For example, a patient living in a remote area requires a rarely☐performed procedure to be conducted. A local dentist A has no direct experience with the procedure. With the smart AR glasses, dentist A can transmit the case data to an experienced dentist B so that dentist B can monitor and observe dentist A's operation, and provide guidance and direction to dentist A through the process. A computing device associated with dentist B allows dentist B to view the procedure broadcasted from dentist A in real time and transmit dentist B's guidance (e.g., notes, written comments) to the smart glasses 100 of dentist A for viewing by dentist A. Such instant smart glasses-mediated communication creates a seamless collaboration to help patients receive needed treatment and care without travel. A similar process may also be applied in warzone scenarios, in which capable field medics are able to perform triage, but are not specifically trained for certain procedures or complications. An overseeing medical doctor in a safe and remote location can talk with the onsite medic through the aforementioned smart glasses-mediated communication, thereby significantly increasing the probability of saving lives.

In examples of dental school or teaching hospitals, a procedure can be performed on a patient and the live view video feed from the smart glasses 100 can be transmitted to an observation room in the same facility or at a remote location. The ability to transmit/stream the video feed allows students to experience a firsthand perspective on how the procedure is performed.

The technology described herein provides a pair of smart glasses 100 to replace traditional loupes/goggles equipped with adjustable optical magnification elements. More specifically, the smart glasses 100 are configured with AR technology for performing procedures and operations in dentistry. With one or more built-in digital cameras, the smart glasses 100 are able to provide varying degrees of magnification. The use of digital cameras also allows the smart glasses 100 to eliminate the need for additional intraoral cameras. The smart glasses 100 provide additional functionality such as capturing and storing still images, recording videos, and broadcasting live views for an audience, which results in greatly-improved documentation, diagnose, and communication with patients, etc. For example, in a teaching hospital/clinic environment, the use of smart glasses 100 makes it extremely convenient for students, fellow doctors/dentists, and administrators to see exactly what a doctor/dentist sees from his angle of view.

Although a pair of smart glasses 100 providing a single magnification may be described in the present disclosure, it should be recognized that eyewear other than a pair of glasses and/or goggles that provide varying degrees of magnification to accommodate various surgical conditions/requirements are also within the scope of the present disclosure. Although the smart glasses 100 are mainly described here in the context of dentistry, it should be recognized that the smart glasses 100 providing similar functionalities may also be used in other areas such as various types of other surgery and examination procedures that are part of medical treatments.

Additionally, to provide the functionality described herein, some implementations of the disclosed smart glasses 100 may have one or more of the following particular physical mechanical characteristics, structure, and components, such as: 12 megapixel auto-focus (12 MP AF) sensor with a lens aperture of f/1.5, optical image stabilization, 2× optical zoom, 16× digital zoom, active-matrix organic light-emitting diode/silicon organic light-emitting diode (AMO-LED/Si-OLED), etc. For example, in one implementation (or in one example), the smart glasses 100 may have a zoom-value in the range of 10×-16×. The camera(s) of the smart glasses 100 may include a sensor with a size of at least 8-12 MP, and record video of at least 1080p @ 60 fps, i.e., a resolution of 1920×1080 pixels and a framerate of 60 fps. It should be recognized that some or all of these components of the smart glasses 100 may be modified or replaced depending on software implementation and mass production needs. However, regardless of specific physical mechanical characteristics, structure and components, the smart glasses described herein are designed such that a built-in camera(s) can be used to replace the fixed optical magnification elements, and a core component/controller including the battery, processor, memory, and other components can help the smart glasses function as intended. In one specific implementation, the core component/controller is a separate device that is connected to the smart glasses.

FIG. 1A is a top plan view of a first implementation of smart glasses 100 in accordance with the present disclosure. In this first implementation, a single camera (See 302 of FIG. 3A) is mounted at the midline/bridge 102 of the smart glasses 100. The smart glasses are a wearable computer glasses that add information alongside or to what the wearer sees. As illustrated, besides the viewing parts and the embedded camera 302 on the front, the smart glasses 100 also include a left-side portion 250 and a right-side portion 202, each of which may contain different components for implementing expected functions of the smart glasses 100, as described further in detail below. The smart glasses 100 may also include a hinge 108 that holds and controls motions of lens 308, prisms 310, LCD electronic shutters 322, and other related parts, as will also be described in detail below. The arrows 2A and 2B in the figure refer to two sides of the smart glasses, which will be described respectively in FIGS. 2A and 2B.

Figure 1B:
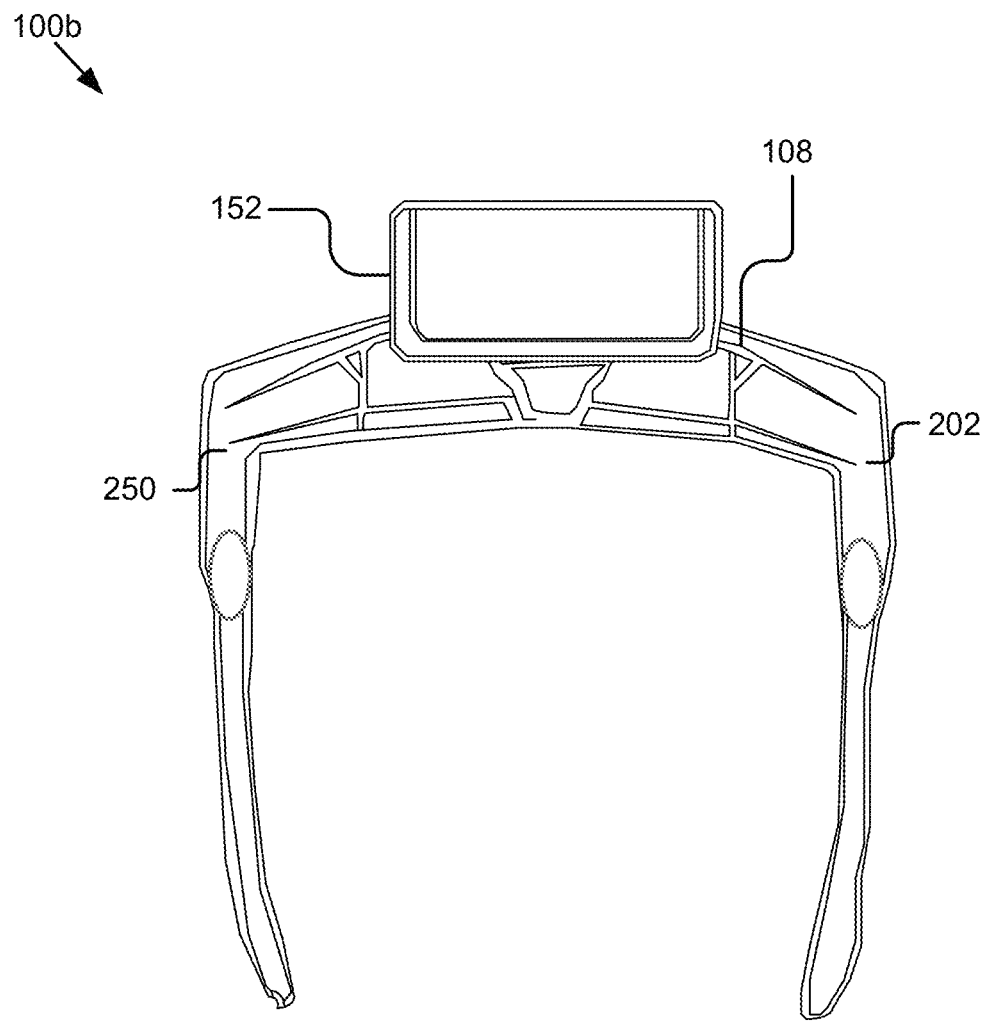
FIG. 1B is a top plan view of a second implementation of the smart glasses with two cameras in accordance with the present disclosure.

FIG. 1B is a top plan view of a second implementation of smart glasses 100b. In this second implementation, two cameras 302 (See 302a and 302b of FIG. 3G) are mounted at the midline/bridge 152 of the smart glasses 100b.

In some implementations, headlamp(s) 304 may also be mounted at the midline/bridge 102/152 of the smart glasses 100a/100b. The headlamp(s) 304 may illuminate an operating field so that a user can perform an operation on real-world objects in the operating field with proper headlight color and brightness when a video/image processing module 522 (described below with reference to FIG. 5) converts the real-world objects seen through the camera(s) 302 into two-dimensional or three-dimensional computer-generated graphics for a display to the user.

Figure 2A:
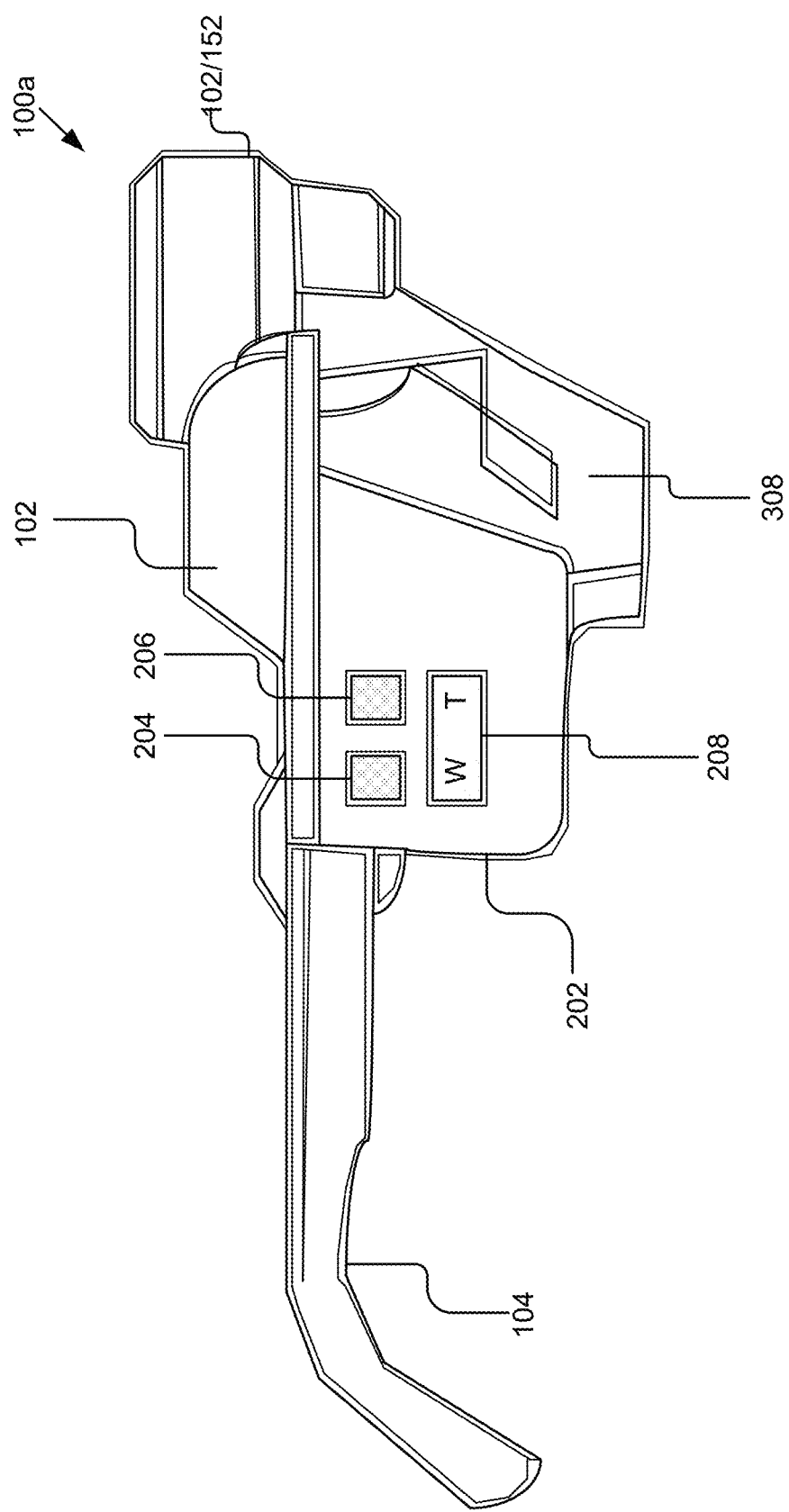
FIGS. 2A and 2B are left-side and right-side views of the first implementation of the smart glasses with a single camera in accordance with the present disclosure.
Figure 2B:
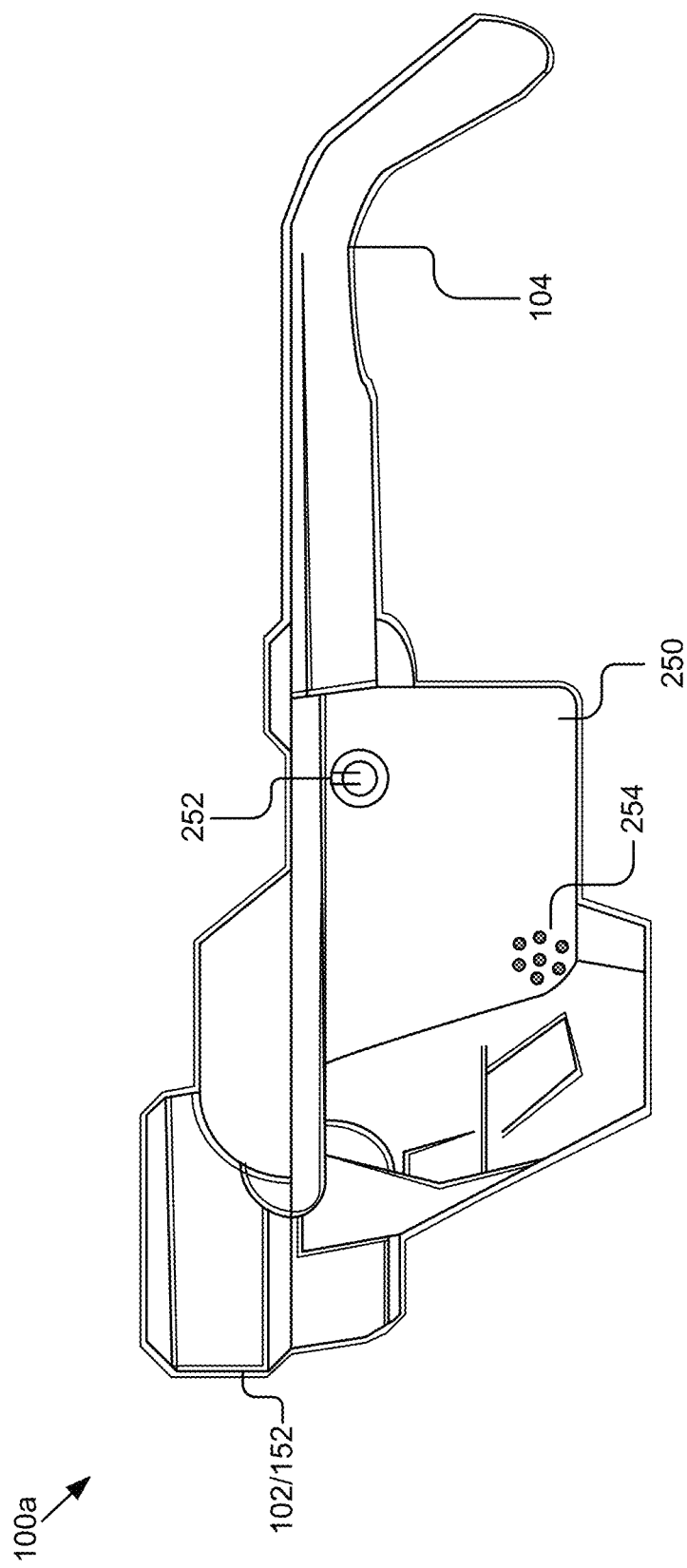

FIG. 2A and FIG. 2B are side views of the first implementation of the smart glasses 100a. In the first implementation, the right-side portion 202 of the smart glasses 100a as shown in FIG. 2A includes a video start/stop button 204, a still image capture button 206, and a telephoto/zoom button 208. A physical touch/non-touch input is received via each of these buttons to invoke an operation. Additionally, as shown in FIG. 2B, the left-side portion 250 of the smart glasses 100a includes a power on/off button 252 to start/stop the operation of the smart glasses 100a, and a microphone 254 to receive an audio input from the user.

Although side views of the smart glasses 100b are not illustrated here, it should be recognized that similar elements that perform similar functionalities may be included in the side portions of the smart glasses 100b. Additionally, although not illustrated, the smart glasses 100a, 100b may also include a speaker for outputting confirmation, setting status, or other information.

Figure 3A:
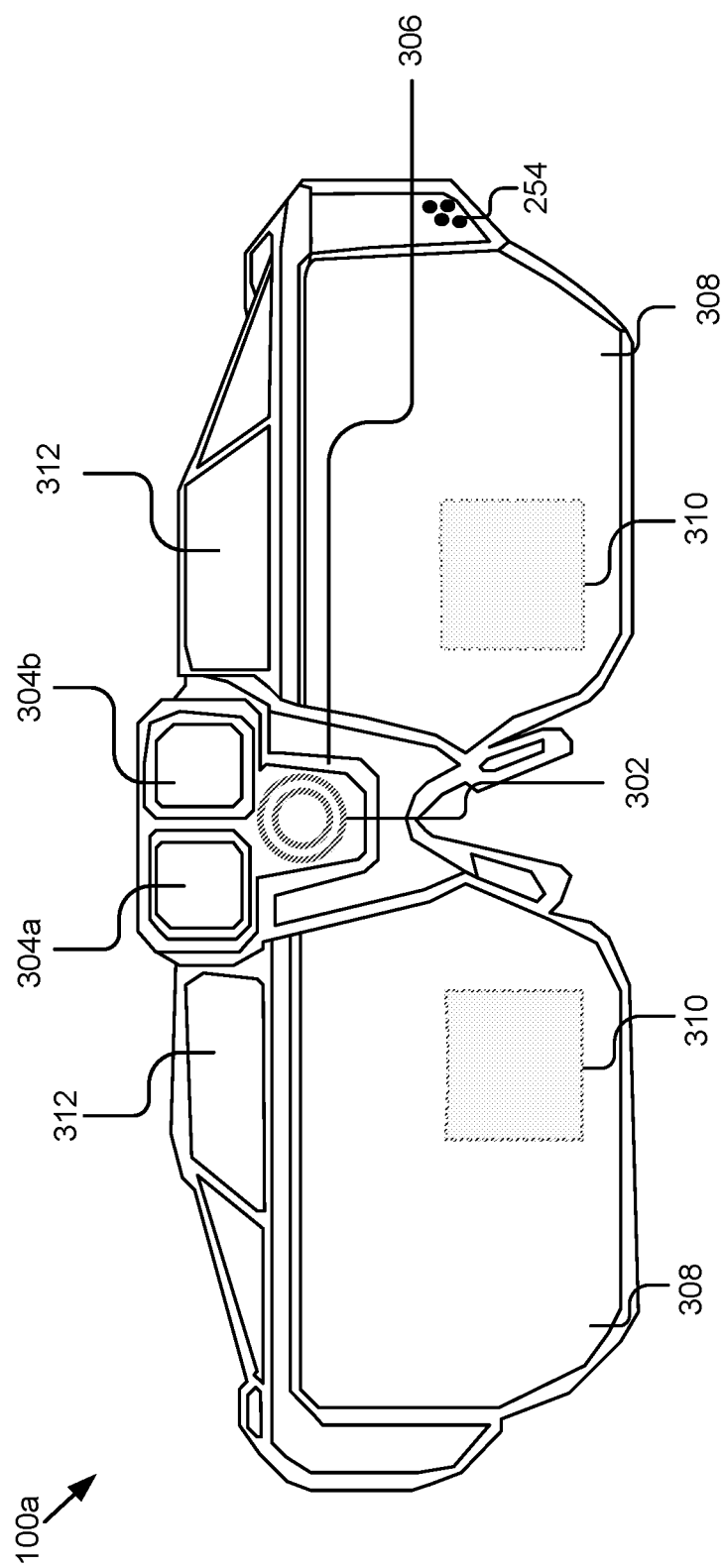
FIG. 3A is a front view of the first implementation of the smart glasses with a single camera in accordance with the present disclosure.

FIG. 3A is a front view of the first implementation of the smart glasses 100a with a single camera 302 in accordance with the present disclosure. In the example of FIG. 3A, the smart glasses 100a include a single camera 302. The camera 302 along with two headlamps 304a, 304b are enclosed in a hinge-mounted member 306 that is mounted near the midline or bridge 102 of the glasses 100a. The hinge mount allows adjustment of the tilt and angle of the camera 302 and headlamps 304a, 304b, for satisfying the operating view of a patient and the fitting of ergonomic comfort needs of the dentist/user.

In the first implementation, the camera 302 is a front-facing high-resolution digital camera that can be turned on/off via voice control. As noted above the camera 302 may include a 12 megapixel auto-focus (12 MP AF) sensor with a lens aperture of f/1.5, optical image stabilization, 2× optical zoom, 16× digital zoom, active-matrix organic light-emitting diode/silicon organic light-emitting diode (AMO-LED/Si-OLED), etc. Additionally, in one implementation, the camera 302 provides a zoom-value in the range of 10×-16×. The camera(s) 302 of the smart glasses 100 may include a sensor with a size of at least 8-12 MP, and record video of at least 1080p @ 60 fps, i.e., a resolution of 1920×1080 pixels and a framerate of 60 fps. For example, a recognition module 524 may recognize a user's voice and convert it into a command to initiate the operation of turning the camera 302 "on" or "off" via a controller unit 412a. The voice/audio input may be received through the microphone 254. Once the camera 302 is on/in operation, the recognition module 524 in communication with the element control module 526 may also convert the user's voice/audio input into other commands to control the camera 302 to perform other functionalities. For example, based on the voice control, the element control module 526 may zoom in/out the camera 302 to adjust the magnification of the view of the surgical/operating field. Additionally, the camera 302 may be controlled by the recognition module 524 and the element control module 526 to capture photographic still images (e.g., for insurance and/or documentation purposes), and also record video of the procedure being performed (e.g., for documentation or educational purposes). In some implementations, the control of the camera 302 may be based on gestures rather than voice. The recognition module 524 and the element control module 526 of the digital camera 302 will be described in detail below with reference to FIGS. 5, 7, and 8.

In some implementations, the headlamps 304 may include a white lamp 304a and an amber lamp 304b that help illuminate the operating field. In dentistry, the white lamp 304a may be used in routine operations while the amber lamp 304b is especially useful when the user is working with light-sensitive resin restorative materials as the amber lamp 304b significantly extends the working time.

The smart glasses 100 in FIG. 3A also include dual monitors 312 and two-piece lens 308 with built-in prisms 310. The dual monitors or displays 312 may be one of a liquid crystal display (LCD), a light emitting diode (LED), an organic light-emitting diode (OLED), or other displays.

Figure 3B:
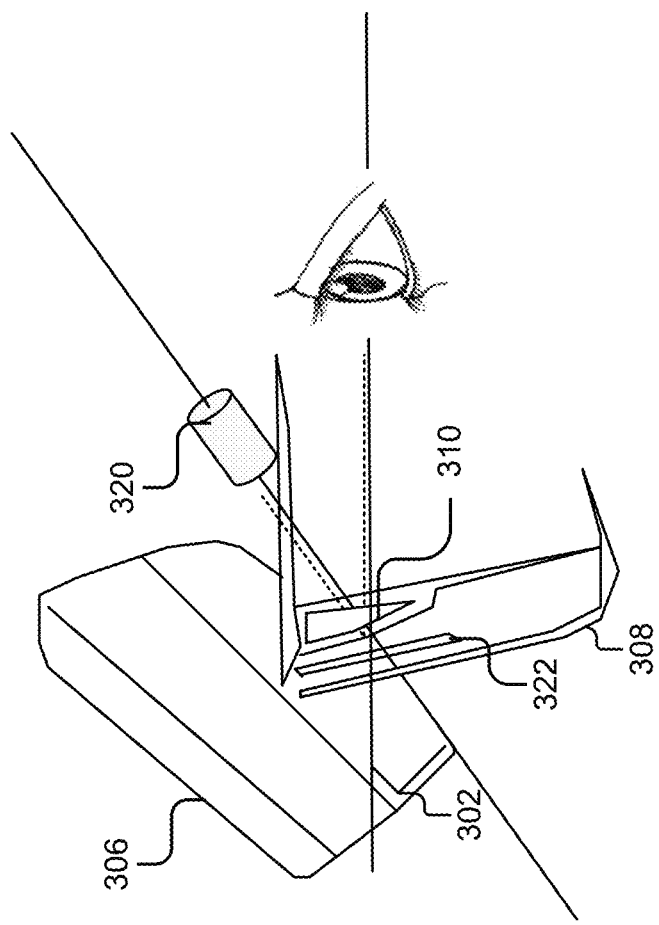
FIG. 3B is a block diagram of the first implementation of the smart glasses for creating a floating image in accordance with the present disclosure.

FIG. 3B is a diagram including example components of smart glasses 100 for creating a floating image. Specifically, when the smart glasses 100 are in operation/on, the digital camera 302 captures images of objects and transmits the image data to micro-projector(s) 320. The micro-projector(s) 320 projects a live view of the object images/data onto a pair of specially☐coated prisms 310 integrated into the lenses. In some implementations, the smart glasses 100 include two micro-projectors 320 and each prism 310 is covered with a reflective coating. The prisms 310, therefore, reflect the projections into the pupils of the wearer of the smart glasses 100, creating the floating images. In some implementations, the position of the prisms 310 is controllable so that the light path can be directed from the micro-projector 320 to the eye of the user. Still more particularly, the element control module 526 controls the position of the prisms 310 and this can be done via voice command or using the foot pedal 418 as will be described below in more detail.

As depicted in FIG. 3B, a liquid crystal light-valve (also referred to as "LCD electronic shutter") 322 is also placed immediately behind each prism 310. In some implementations, an LCD electronic shutter control module 812 (described below in FIG. 8) controls the LCD electronic shutter 322 to change its translucency/opacity to provide a darker background/contrast for better image protection/viewing. When the smart glasses 100a are not in operation (i.e., turned off), the prisms 310 and the LCD electronic shutters 322 will become transparent, which then allows the glasses wearer to see through the prisms 310 and the LCD electronic shutters 322 without any obstruction and distortion.

Figure 3C:
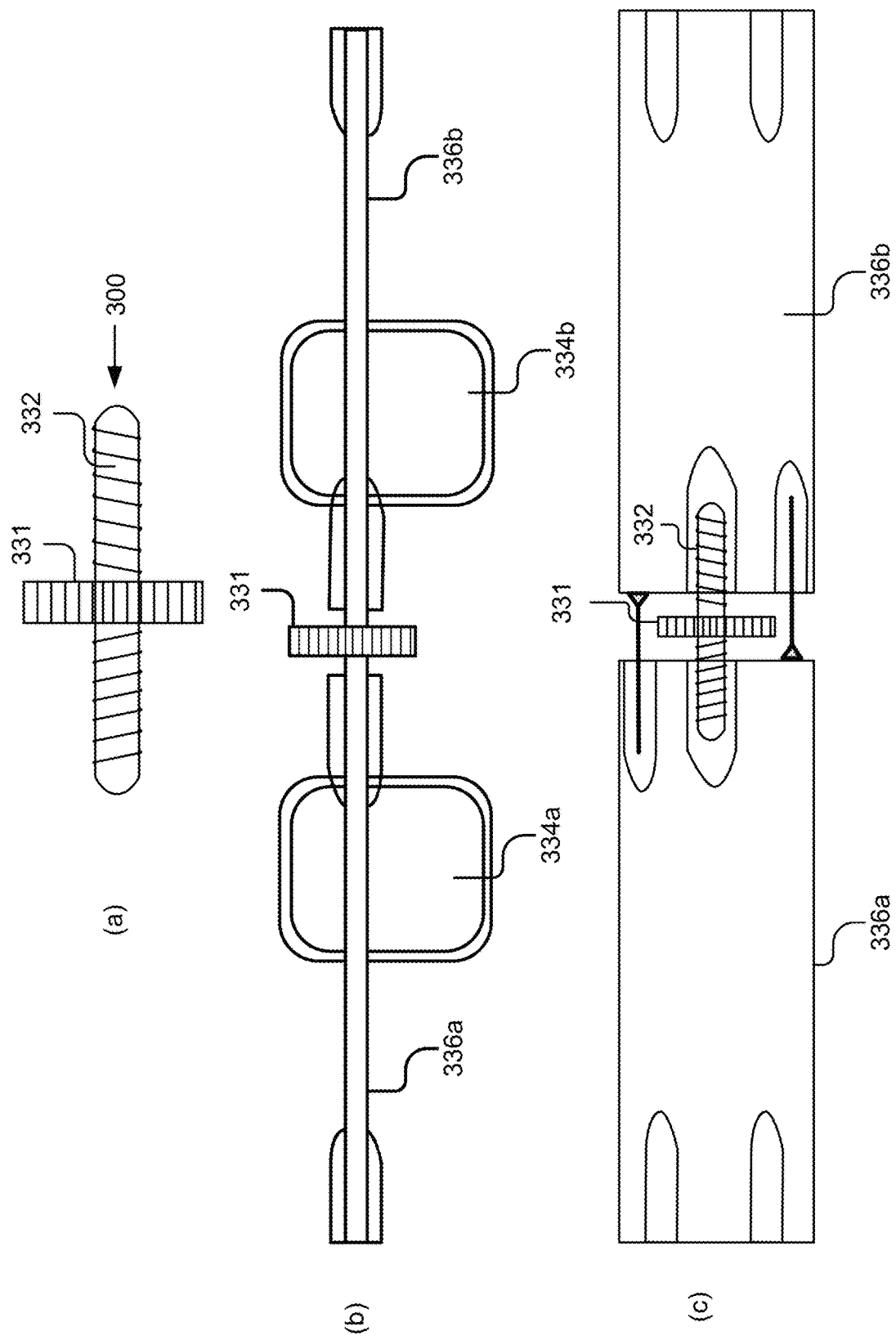
FIG. 3C is an example inner framework of smart glasses for adjusting an interpupillary distance in accordance with the present disclosure.

FIG. 3C depicts an example inner framework of smart glasses 100 for adjusting an interpupillary distance (IPD). The interpupillary distance (IPD) is the distance measured between the centers of the pupils of the eyes of a user. This distance is different from person to person and also depends on whether they are looking at near objects or far away. Optionally, for the smart glasses 100a with two prisms 310 for projecting camera-captured images to glasses wearer's eyes, the IPD with respect to the two prisms 310 optimally is adjustable for different users.

Part (a) of FIG. 3C shows a dial screw 330 including a wheel 331 and counter-rotational threads 332. A user may use the dial screw 330 to change and customize the IPD to his/her preferred distance. In some implementations, the micro-projectors 320, prisms 310, LCD electronic shutters 322, and/or lenses 308 are respectively enclosed in two housing members 334a and 334b mounted onto two inner framework plates 336a and 336b connected via the dial screw 330. Part (b) of FIG. 3C shows a front view of the inner framework plates 336a and 336b that hold two housing members 334a and 334b, respectively. Part (c) of FIG. 3C shows a top view of the inner framework plates 336a and 336b connected by the dial screw 330. By adjusting the wheel 331 on the counter rotational threads 332, a user may narrow or widen the distance between the two inner framework plates 336a and 336b, thus changing the viewing angle to accommodate the IPD variations. The design of FIG. 3C allows end users to easily adjust and customize the IPD manually or automatically with commands or instructions, which does not require a customer to specifically design and manufacture his/her own pairs of smart glasses 100, as most glasses services currently do. Therefore, the design exhibited by FIG. 3C facilitates automation and mass production of the smart glasses 100, thereby reducing cost and time for customers.

Figure 3D:
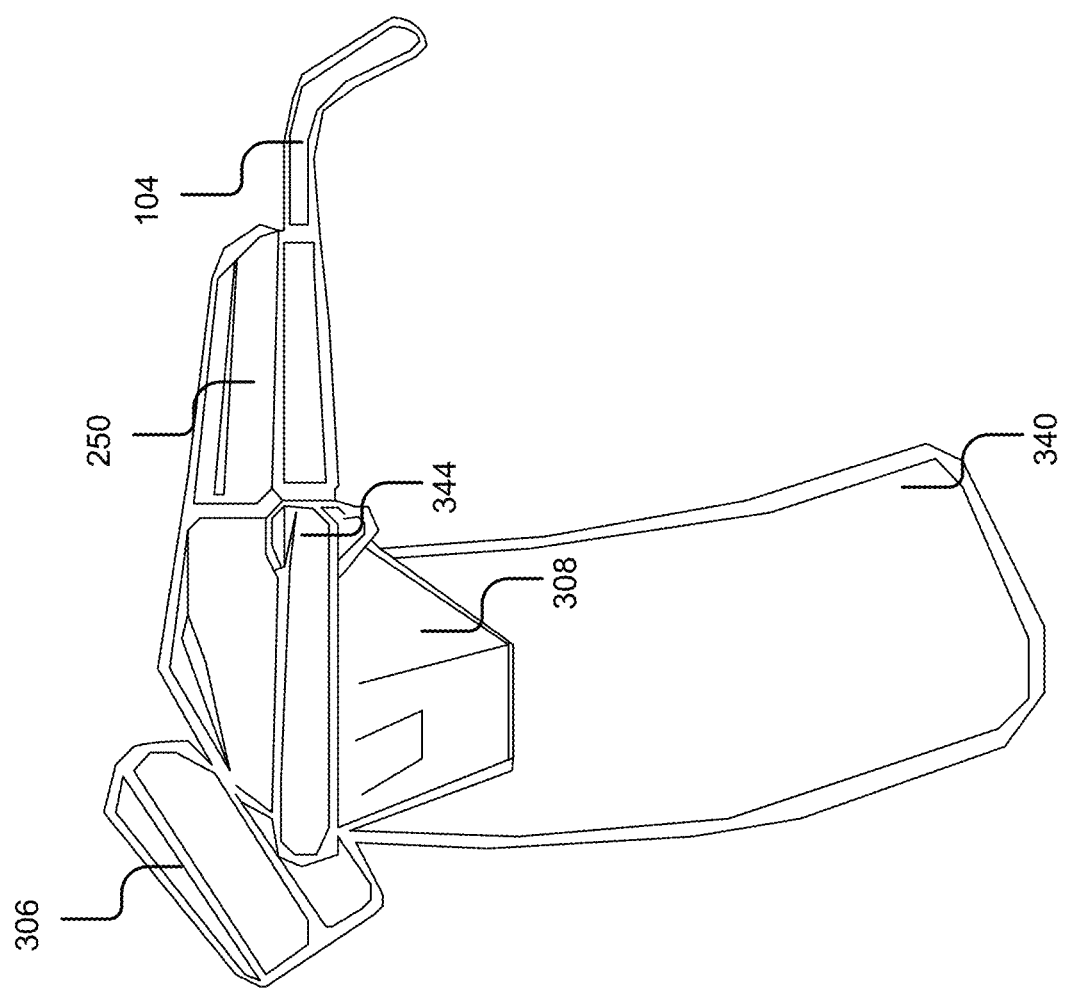
FIGS. 3D and 3E are example protection layers of the smart glasses in accordance with the present disclosure.
Figure 3E:
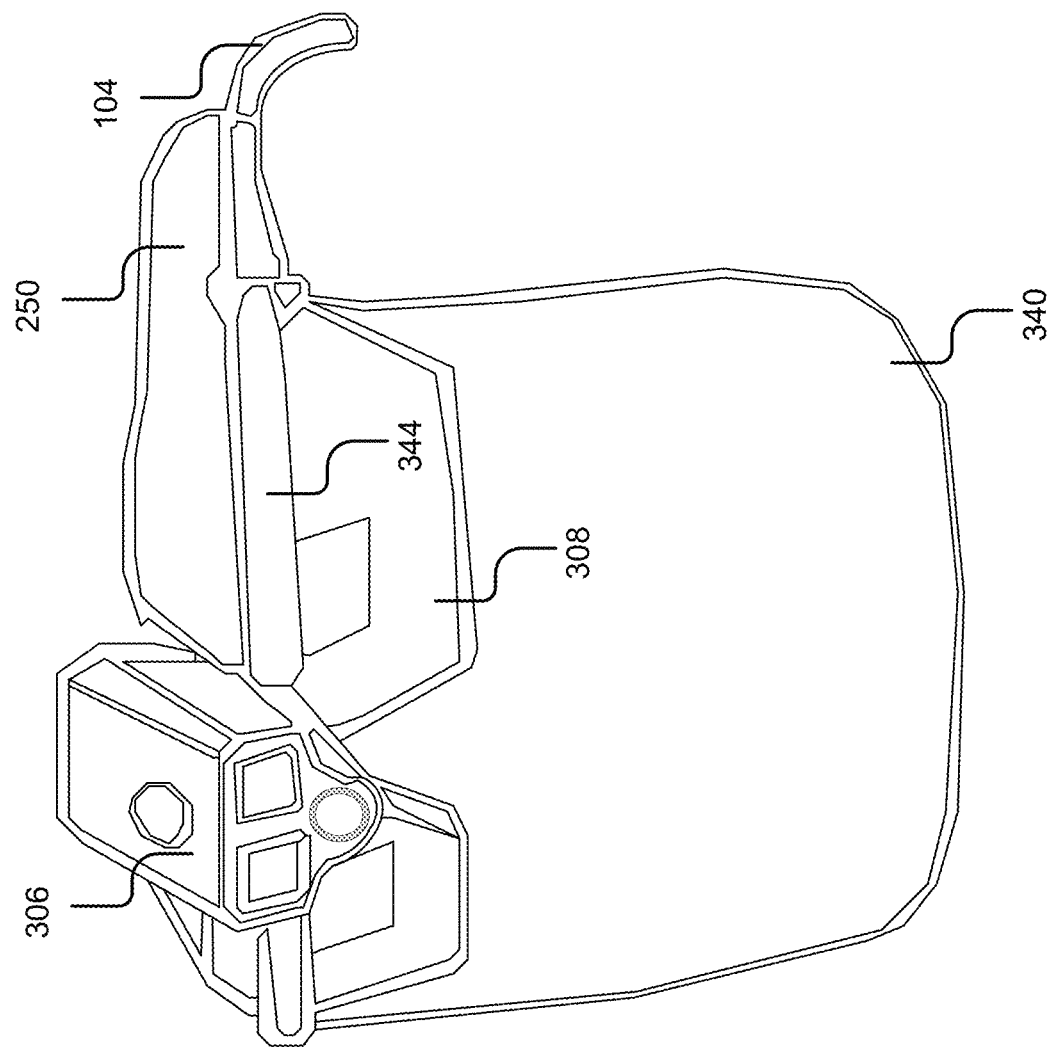

FIGS. 3D and 3E depict example optional protection layers of the smart glasses 100a. The protection layer 340 may include one or more layers of protection against aerosolized contaminants. The protection layer 340 may be made of materials that are recyclable, and accordingly, the protection layer 340 is disposable and replaceable after each use. In some implementations, the protection layer 340 may be also reusable after certain decontamination, sanitization, and/or other proper treatments. The protection layer 340 is illustrated in the following as a face shield, although other types of protection layers known in the art are also considered in the present disclosure. In some implementations, the top periphery of the protection layer 340 may have a metal or magnetic strip 342 attached there to so that will be held in place by magnetic arms 344 as will be described below. FIG. 3D is a side view of the smart glasses 100a with a face shield 340. FIG. 3E is a ¾ view of the smart glasses 100a with an attached face shield 340. The face shield 340 is used as an added layer of protection against aerosolized contaminants.

Figure 3F:
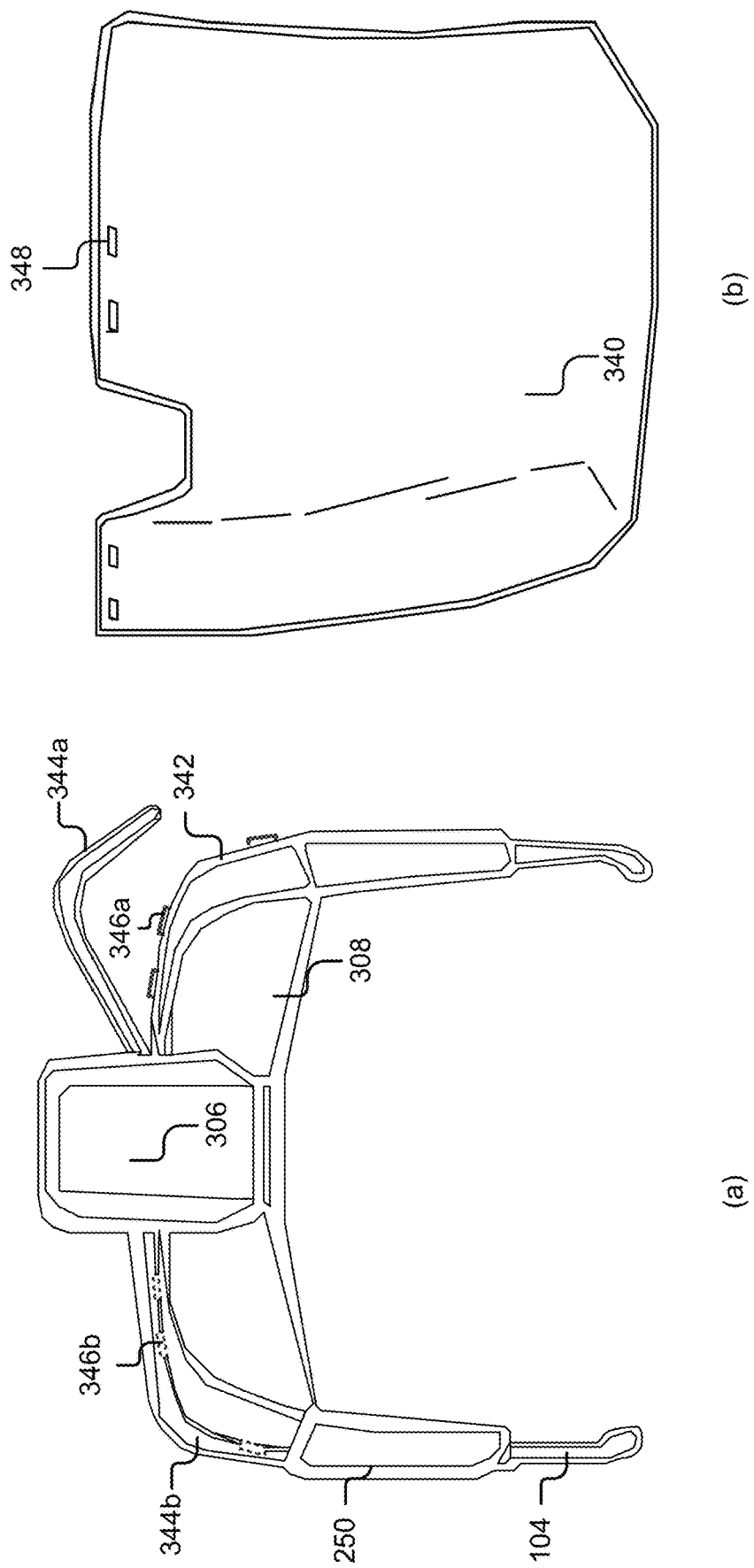
FIG. 3F is a top plan view of the smart glasses with an example holding portion in an open position and a perspective view of an example protection layer alone in accordance with the present disclosure.

FIG. 3F shows components of the smart glasses 100a that hold the face shield 340 in part (a) and a stand-alone face shield in part (b). As depicted in part (a), the smart glasses 100a are equipped with a magnetic strip(s) 342 and two hinged magnetic arms 344a, 344b. The two hinged arms 344a, 344b are connected near the midline of the outer frame of the smart glasses 100a. The hinged arms 344a, 344b may swivel open and closed. When the glasses wearer repositions the hinged arms 344a, 344b from an open position to the closed position, the hinged arms 344a, 344b lock together magnetically with the magnetic strip(s) 342 to hold the face shield 340 in place.

Besides the magnetic strip(s) 342 and the hinged magnetic arms 344, in other implementations, additional or other mechanisms that facilitate the holding the face shield 340 to the smart glasses 100a are also included. For instance, in one implementation, the smart glasses framework may include multiple protrusions 346 that fit slots 348 on a face shield 340 for proper alignment. For instance, in part (a) of FIG. 3F, three protrusions 346b and three protrusions 346a are disposed on the smart glasses' framework (or on the magnetic strip(s) 342 under certain circumstances). Correspondingly, in part (b) of FIG. 3F, multiple slots 348 may be disposed on top periphery of a face shield for attachment of the face shield 340 to the smart glasses 100a. Part (b) of FIG. 3F depicts a perspective view of a standalone face shield 340, on which there are five visible slots 348 with one slot invisible from the perspective view. It should be noted that the shape, size, and number of slots 348 and corresponding protrusions 346 illustrated in the figure are merely one example. In practical applications, any number, size, and shapes of corresponding slots 348 and protrusions 346 that facilitate the holding of the face shield 340 to the smart glasses 100a are considered in the present disclosure.

The design shown in FIGS. 3D, 3E, and 3F provides ease of use and ease of replacement in replacing an inexpensive plastic face shield. This feature also allows a user to quickly and easily remove a face shield 340 for certain procedures that do not require extra protection, thereby reducing bulk and weight and improving user experience.

Figure 3G:
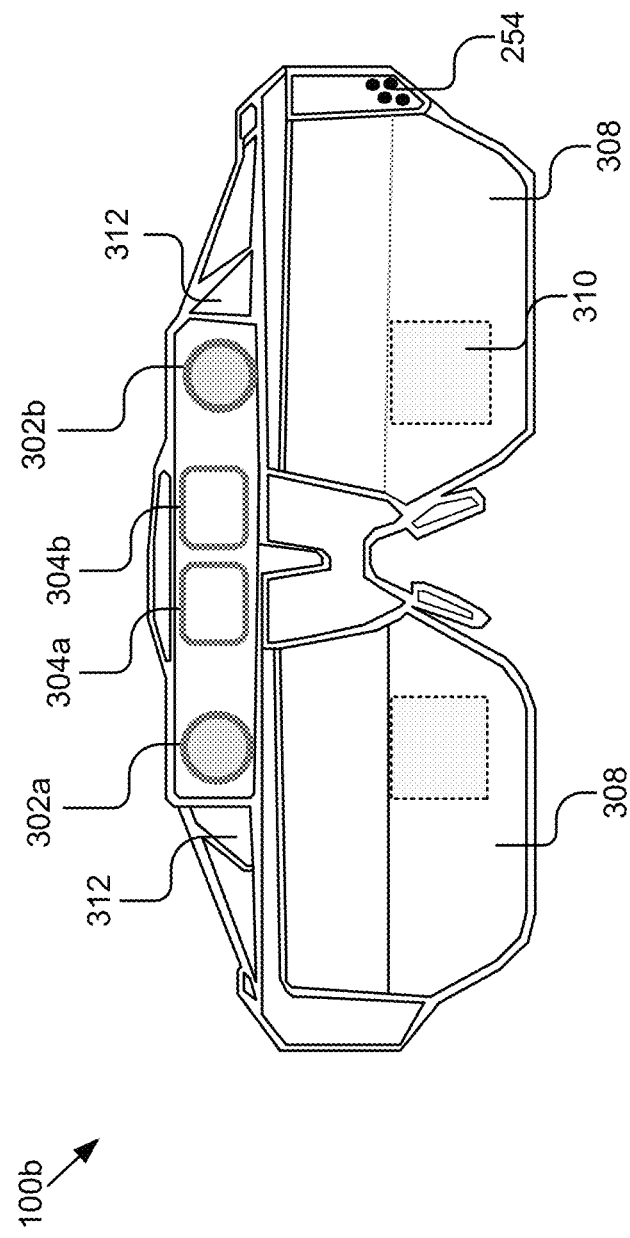
FIG. 3G is a front view of the second implementation of the smart glasses with two cameras in accordance with the present disclosure.

In addition to the smart glasses 100a equipped with a single centrally-located camera 302 shown in FIG. 3A, a second implementation of the smart glasses 100b with two cameras 302a, 302b, in accordance with the present disclosure is shown in FIG. 3G. The smart glasses 100 of FIG. 3A may utilize the single centrally-located camera to broadcast a same image to both LED/LCD monitors, while the smart glasses 100b of FIG. 3G may utilize two separate cameras 302 to simulate true binocular vision. Other than this difference, the smart glasses 100b of FIG. 3G may possess similar characteristics and perform similar functionalities as described in FIGS. 3B-3F with reference to the smart glasses 100a of FIG. 3A.

Figure 4:
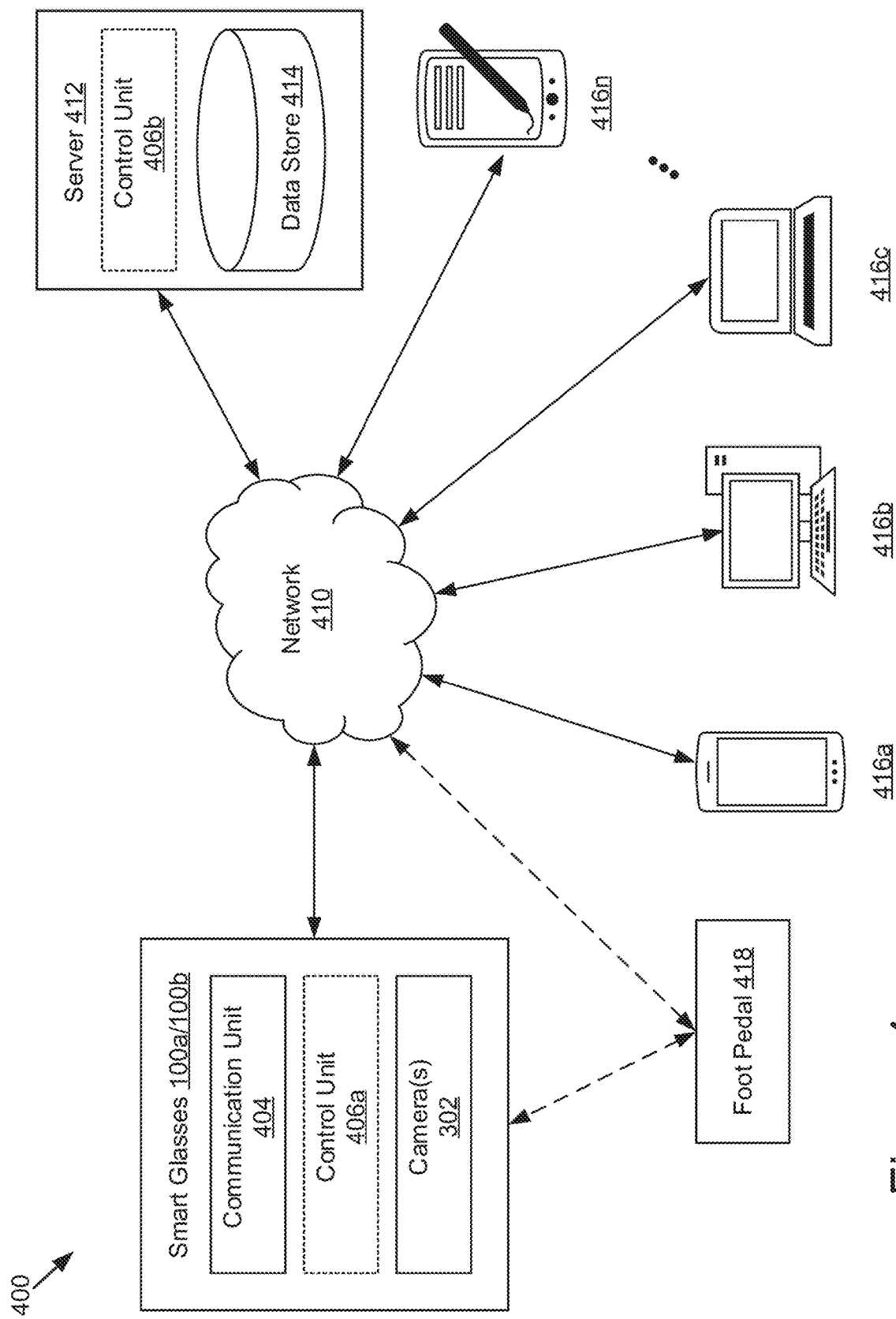
FIG. 4 is a block diagram of a first implementation of a system for using smart glasses in dentistry in accordance with the present disclosure.

FIG. 4 is a block diagram of a first implementation of system 400 for using smart glasses 100a and 100b (together referred to as "smart glasses 100") in dentistry. It should be noted that the system 400 may also be used in other medical practices or other fields (e.g., banks, security check). As depicted, the system 400 includes smart glasses 100, a server 412, user devices 416a . . . n, and a foot pedal 418, which are coupled to each other via a network 410.

In some implementations, the smart glasses 100 include a communication unit 404, a control unit 406a, and camera(s) 302. The smart glasses 100 may either be the smart glasses 100a in FIG. 3A or the smart glasses 100b in FIG. 3G. The communication unit 404 includes hardware to communicate the smart glasses 100 to other entities of the system 400 for receiving and transmitting data via the network 410. In some implementations, the communication unit 404 allows the smart glasses 100 to link to the server 412, user devices 416a . . . n, and foot pedal 418 through a wireless connection. The communication unit 404 will be described in detail below with reference to FIG. 5.

The control unit 406a includes the components required for performing the functionality such as displaying images, adjusting the cameras 302 and headlamps 304 through voice control, recording a video, etc. Although the control unit 406a resides locally in the smart glasses 100, a control unit 406b may be separate from the smart glasses 100 to reduce the weight placed on the nose and ears of the wearer of the smart glasses 100. Therefore, the control unit 406a is depicted in dashed lines to indicate that there may be other control units (e.g., control unit 406b) residing remotely on other entities of the system 400 (e.g., the server 412). The components of the control unit 406a will be described in more detail below with reference to FIGS. 5-8.

The camera(s) 302 is a high-resolution digital camera(s) that corporates with the communication unit 404 and the control unit 406a to capture, record, and store image/video data. For example, the camera(s) 302 may have at least a 12 megapixel resolution to adequately provide the video recording with a resolution of 3840×2160 pixels that is displayed 60 times per second (i.e., 4 k/60 fps). The camera(s) 302 with other parameters are also contemplated. The camera(s) 302 is also capable of providing optimal zoom, digital zoom, and stabilization, etc.

The camera(s) 302 may be a single centrally-positioned digital camera 302 as depicted in FIG. 3A. Alternatively, the camera(s) 302 may include multiple cameras 302a and 302b in FIG. 3G. The camera(s) 302 can be mounted on a hinge 108 of the smart glasses 100 for easy adjustment of the angle and tilt of the camera(s) 302 and corresponding parameters such as the view angle. In some implementations, the camera(s) 302 stores the images and video in a built-in microSD card of the smart glasses 100. In other implementations, the camera(s) 302 transmits the video/image data to the server 412 for storing on the data store 414.

The server 412 may be either a hardware server, a software server, or a combination of software and hardware. The server 412 may be also a cloud virtual server. The server 412 may be, or may be implemented as, a computing device including a processor, a memory, applications, a database, and network communication capabilities. In particular, the server 412 may include a control unit 406b and a data store 414. The control unit 406b performs similar functionality as the control unit 406a. The data store 414 stores video data, audio data, user data, and other types of data received from the smart glasses 100, user devices 416a . . . n, and foot pedal 418.

The data store 414 may store data associated with a database management system (DBMS). For example, the DBMS may include a structured query language (SQL) DBMS, a NoSQL DMBS, various combinations thereof, etc. In some instances, the DBMS may store data in multi-dimensional tables comprised of rows and columns, and manipulate, e.g., insert, query, update and/or delete, rows of data using programmatic operations.

The user devices 416a . . . n (collectively may be referred to as "user device 416") may be any type of computing device associated with a user. The user may exchange data with the wearer of the smart glasses 100 or access the data stored in the server 412 using the user device 416. For example, a doctor may access his/her desktop or tablet computer to send real-time instructions to a doctor wearing the smart glasses 100 and performing an operation on a patient. Or an audience may use his/her mobile phone to ask a question to a professor wearing the smart glasses 100 via voice communication. Or a patient may use a laptop computer to retrieve his/her X-ray image stored in the data store 414 of the server 412. In some implementations, a user device 416 is a device for displaying live video in a dentist's office during a procedure, so that a patient and the dentist can see the same thing at the same time.

The foot pedal 418 is a device that enables a user to control any aspect of the system 400 or the smart glasses 100. For example, foot pedal 418 can be used by the dentist to control dictation playback with his/her foot in medical transcription. The user may play, rewind, and fast forward by tapping different sections of the foot pedal 418 with his/her foot. In the dentistry cases using the smart glasses 100, the foot pedal 418 may be used by a dentist wearing the smart glasses 100 to send commands to the smart glasses 100 as part of the control of the smart glasses 100, for example, to control the capture of images/video by the camera(s) 408, to adjust cameras 302 (e.g., zoom, left, right, etc.), to control other parts of the smart glasses 100 as described elsewhere herein. The foot pedal 408 could be any pedal controlled by a dentist, dentist assistant, or another relevant person.

In some implementations, the foot pedal 418 may have a computer interface, for example, a universal serial bus (USB) port, to couple with the smart glasses 100 or the server 412 with a wired cable. In other implementations, the foot pedal 418 may communicate with the other entities of the system 400 through a wireless connection.

The network 410 can be a conventional type, wired or wireless, and may have numerous different configurations including a star configuration, token ring configuration or other configurations. Furthermore, the network 410 may include a local area network (LAN), a wide area network (WAN) (e.g., the Internet), and/or other interconnected data paths across which multiple devices may communicate. In some implementations, the network 410 may be a peer-to-peer network. The network 410 may also be coupled to or include portions of a telecommunications network for sending data in a variety of different communication protocols. In some implementations, the network 410 may include Bluetooth communication networks or a cellular communications network for sending and receiving data including via short messaging service (SMS), multimedia messaging service (MMS), hypertext transfer protocol (HTTP), direct data connection, wireless application protocol (WAP), email, etc.

Although FIG. 4 illustrates one network 410 coupled to the smart glasses 100, the server 412, the user device 416, and the foot pedal 418, in practice one or more networks 410 can be connected to these entities. In a typical implementation, the smart glasses 100 may communicate with other entities of the system 400 via a wireless network 410 such as a Wi-Fi network, a Bluetooth communication network, a cellular communication network for receiving and sending data.

Figure 5:
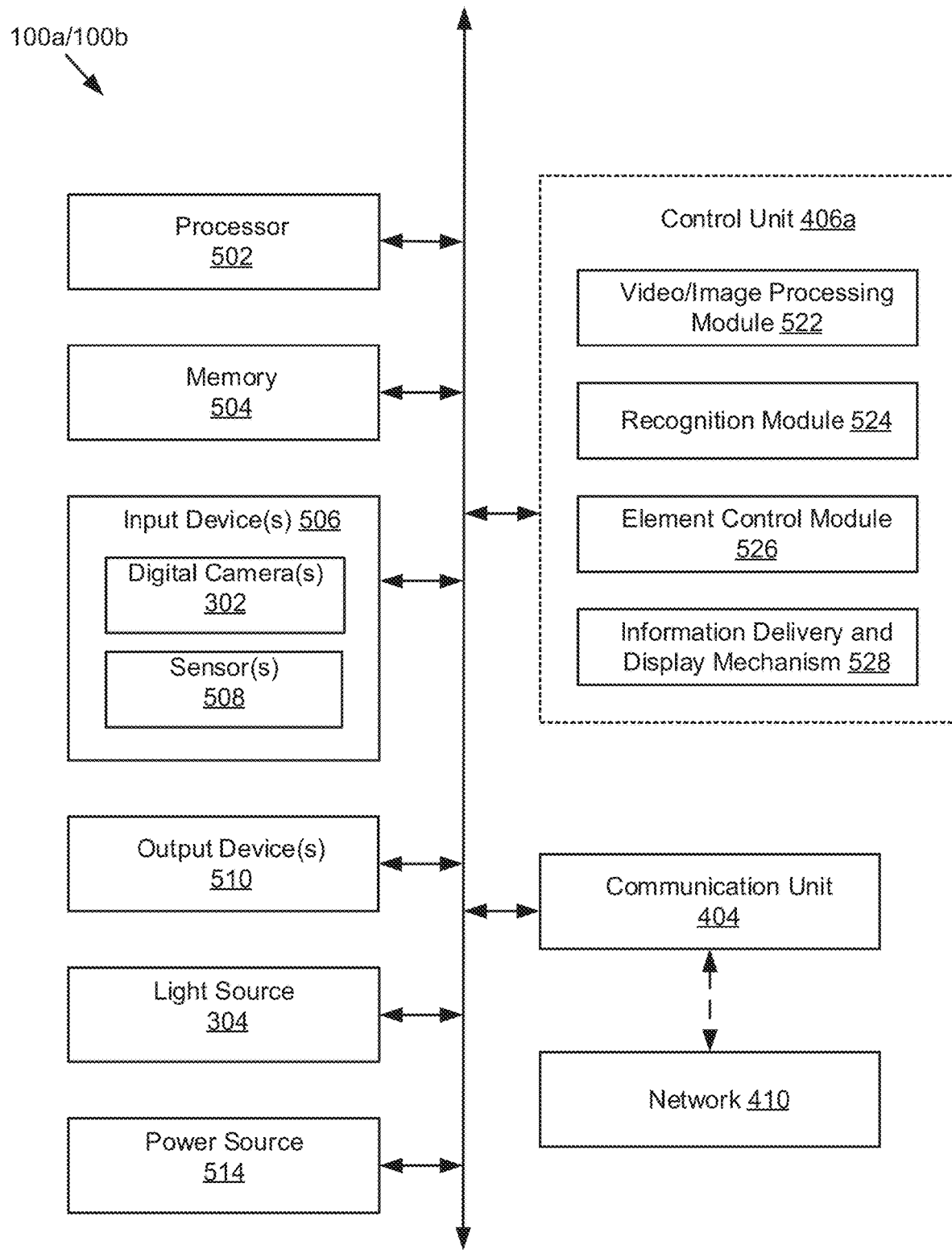
FIG. 5 is a block diagram of one implementation of smart glasses in accordance with the present disclosure.

FIG. 5 is a block diagram of example components of the smart glasses 100 of FIG. 4. As depicted, the smart glasses 100 may include a processor 502, a memory 504, one more input devices 506, one or more output devices 510, a light source 304, a power source 514, a control unit 406a, and the communication unit 404 that connects the smart glasses 100 to the network 410. The smart glasses 100 depicted in FIG. 5 are provided by way of example and it should be understood that the glasses 402 may take other forms and include additional or fewer components without departing from the scope of the present disclosure. For instance, various components of the smart glasses 100 may be coupled for communication using a variety of communication protocols and/or technologies including, for instance, communication buses, software communication mechanisms, computer networks, etc. While not illustrated, the smart glasses 100 may include various operating systems, sensors, additional processors, and other physical configurations. The processor 502, memory 504, etc., are representative of one or more of these components.

The components 506, 510, 304, 514, 404, and/or 406a may be communicatively coupled by a bus 550 and/or the processor 502 to one another and/or other components of the smart glasses 100. In some implementations, the components 506, 510, 304, 514, 404, and/or 406a may include computer logic (e.g., software logic, hardware logic, etc.) executable by the processor 502 to provide their acts and/or functionality. In any of the foregoing implementations, these components 506, 510, 304, 514, 404, and/or 406a may be adapted for cooperation and communication with the processor 502 and the other components of the smart glasses 100.

The processor 502 may execute software instructions by performing various input, logical, and/or mathematical operations. The processor 502 may have various computing architectures to process data signals (e.g., CISC, RISC, etc.). The processor 502 may be physical hardware and/or virtual and may include a single core or plurality of processing units and/or cores. In some implementations, the processor 502 may be coupled to the memory 504 to store data therein and access data and instructions stored therein. The processor 502 may also be coupled to other components of the smart glasses 100 including, for example, the input device 508, the output device 510, the communication unit 404, and the control unit 406a.

The memory 504 may store and provide data access to the other components of the smart glasses 100. In some implementations, the memory 504 may store instructions and/or data that may be executed by the processor 502. The memory 504 is also capable of storing other instructions and data, including, for example, an operating system, hardware drivers, other software applications, databases, etc.

The memory 504 may include a non-transitory computer-usable (e.g., readable, writeable, etc.) medium, which can be any non-transitory apparatus or device that can contain, store, communicate, propagate or transport instructions, data, computer programs, software, code, routines, etc., for processing by or in connection with the processor 502. In some implementations, the memory 504 may include one or more of volatile memory and non-volatile memory (e.g., RAM, ROM, hard disk, optical disk, etc.). For example, the memory 504 may include secure digital (SD) card(s). It should be understood that the memory 504 may be a single device or may include multiple types of devices and configurations.

In some implementations, the communication unit 404 may include one or more interface devices (I/F) for wired and wireless connectivity to the other entities and/or components of the system 400 or other entities and/or components external to the system 400 such as third-party servers, networks, or other systems. For instance, the communication unit 404 may include, but is not limited to, various types of known connectivity and interface options. The communication unit 404 can provide connections to other entities of the system 400 using various standard communication protocols. For instance, the communication unit 404 may include, but is not limited to, cable interfaces (e.g., CAT-5), wireless transceivers for sending and receiving signals using Wi-Fi™, Bluetooth®, cellular communications, etc., universal serial bus (USB) interfaces, various combinations thereof, etc. The communication unit 404 may be coupled to a network such as a network 410. In some implementations, the communication unit 404 can link the processor 502 to the network 410 which may in turn be coupled to other processing systems. The communication unit 404 can provide other connections to the network 410 and to other entities and systems using various standard communication protocols, including, for example, those discussed elsewhere herein.

The input device(s) 506 may include any device for inputting information into the smart glasses 100. In some implementations, the input device(s) 506 includes camera(s) 302 and sensors 508. The camera(s) 302 is a high-resolution (e.g., 1920×1080 pixels, 3840×2160 pixels) camera that can capture still images and record a video. The camera(s) 302 may also support a live view function so that a user can view the video/image in real time. In some implementations, the camera(s) 302 operates with a command from the foot pedal 418, from the voice of a wearer of the smart glasses 100, or from the gesture of the wearer.

In some implementations, the sensors 508 may include one or more audio input devices (e.g., microphone) that capture audio signals in the environment in which the smart glasses 100 are used for further processing. For example, an audio input device signals the recognition module 524 included in the control unit 406a to perform voice recognition and further to activate a "hands-free" operation by the wearer of the smart glasses 100.

In some implementations, the sensors 508 may include one or more light sensors that detect the ambient light conditions to provide control for display. For example, a light sensor may communicate with an element control module 526 included in the control unit 406a to provide information for changing the brightness or color to accommodate the needs of an operating field associated with the wearer of the smart glasses 100.

The audio input devices and light sensors are only examples of the sensors 508. It should be understood that any other type of sensors 508 that obtain information useful for the operation of smart glasses 100 may also be contemplated.

The output device 510 may be any device capable of outputting information from the smart glasses 100. The output device 510 may be any one or more of a monitor or display 312 (LCD, LED, OLED, etc.) and a speaker. In addition to the built-in output device 510, in some implementations, the smart glasses 100 also communicate with one or more external output devices via the communication unit 404 for presenting information simultaneously on the external output device(s). For example, in a scenario where a professor is performing an operation, a live view video about the procedures and operations that the professor is conducting will be explained and demonstrated to the audience using a big-screen monitor and speaker external to the smart glasses 100.

The light source 304 may be an illumination device that can be selectively activated responsive to a voice command or a foot-pedal command. In some implementations, the light source 304 includes a white headlamp 304a and an amber headlamp 304b. These headlamps 304 together with the camera(s) 302 are mounted on a hinge 108 of the smart glasses 100 so that the viewing angle of a user can be adjusted to improve user ergonomics. A user may be a dentist, a surgeon, etc., who uses the headlamps 304 to illuminate his/her operating/working field. It should be noted that a white headlamp 304a and an amber headlamp 304b are merely examples of the light source, and other light sources such as an ultraviolet light source, an infrared source, etc., are possible.

The power source 514 may include a main battery that provides power to the components of the smart glasses 100. In some implementations, the main battery is rechargeable and/or swappable. For example, the main battery may be a long lasting and secure battery that can be easily accessed or replaced. In some implementations, the main battery may be charged wirelessly to allow long working time (e.g., eight hours per day) and to prevent down time due to depleted battery levels. In other implementations, the power source 514 may include an additional backup battery, which may provide power supply when the main battery is swapped out and replaced. This then will not allow a procedure to pause due to the loss of power.

Although the depicted control unit 406a is included in the smart glasses 100 in FIG. 5, in some implementations, the control unit 406a may be remote or located on one or more devices separate from the smart glasses 100 for at least purpose of weight reduction and heat management. The smart glasses 100 may be wired with a separate device, for example, through a USB connection. The smart glasses 100 may also be wirelessly connected with the separate device through a Wi-Fi network, a Bluetooth communication network, a cellular communication network.

When the core operating components including the control unit 406a are remotely located, for example, on the server 412, the smart glasses 100 and the server 412 are able to divide or partition processing responsibility such that the smart glasses 100 are responsible primarily for interacting with a user and collecting information. The server 412 is primarily responsible for storage of data, assisting the smart glasses 100 with the processing of information, and facilitating faster communication with other entities (e.g., the user device 416). It should be understood that there may be a variety of other divisions of functions between the smart glasses 100, the server 412, and/or other backend sources (not shown).

The control unit 406a performs analysis, computation, and control of the smart glasses 100 to assist a dentist with performing dentistry tasks or procedures. For example, the control unit 406 may activate the camera/glasses with user-specific settings of a dentist upon receiving a user-initiated request from the dentist for a specific operation (e.g., conducting an operation). The control unit 406 may dynamically control camera/glasses during the specific operation, monitor the progress of the specific operation, and generate overlays indicating the progress of the specific operation for display to the wearer of the smart glasses 100. Once the specific operation completes, the control unit 406a may deactivate/stop the live view camera as well as the smart glasses 100.

In some implementations, the control unit 406a comprises a video/image processing module 522, a recognition module 524, an element control module 526, and an information delivery and display mechanism 528.

The video/image processing module 522 includes hardware, software, and/or firmware for communicating with the camera(s) 302 to receive and analyze image/video data and to generate at least one image and video for display to the wearer of the smart glasses 100 and other viewers. The video/image processing module 522 will be described in more detail below with reference to FIG. 6.

The recognition module 524 includes hardware, software, and/or firmware for performing various recognition process on received data. For example, the recognition module 524 may perform audio recognition on a voice command received from the glasses wearer or audio data received from other viewers. The recognition module 524 may also perform video recognition on the image/video data received from the camera(s) 302. The recognition module 524 may further perform facial recognition on a patient's portrait image, or other types of pattern recognition on other types of data. The recognition module 524 will be described in more detail below with reference to FIG. 7.

The element control module 526 includes hardware, software, and/or firmware for controlling or adjusting an element of the smart glasses 100 responsive to receiving a control command. For example, the element control module 526 may control the operation of the camera(s) 302. The element control module 526 may also be used to turn on/off the light source/headlamp 304 and control the light intensity of the operating light source 304. The element control module 526 may control micro-projectors 320 to adjust an angle of projection and control the LCD electronic shutters 322 to turn on or turn off. The control command may be a voice command, a foot-pedal command, or a gesture command, etc. The element control module 526 will be described in more detail below with reference to FIG. 8.

The information delivery and display mechanism 528 includes hardware, software, and/or firmware for cooperating with the output device 510 and other components of the smart glasses 100 for performing in-eye projection of images and displaying images in two-dimension or three-dimension. In some implementations, the information delivery and display mechanism 528 may communicate with built☐in LCD/LED/OLED projectors to project a video/image from the camera(s) 302 for display on the output device 510. In some implementations, the information delivery and display mechanism 528 may overlay instructions or notes from a remote doctor on the monitor or display 312 of the smart glasses 100 for viewing by the glasses wearer, or overlay medical information such as an X-ray record on the monitor or display 312 of the smart glasses 100 for viewing by the glasses wearer.

Figure 6:
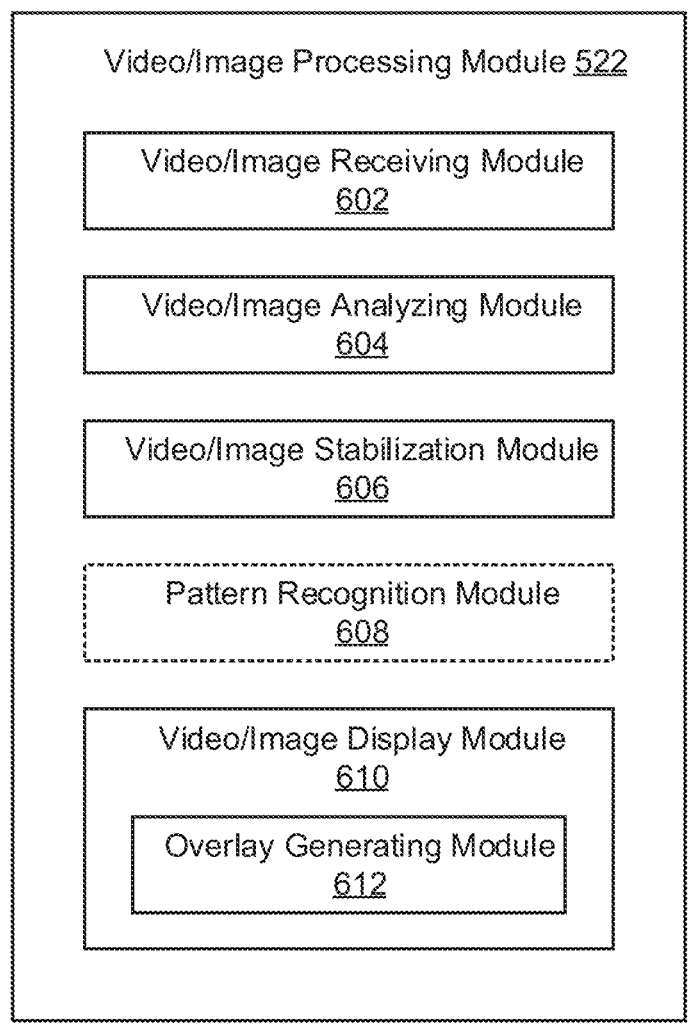
FIG. 6 is a block diagram of one implementation of a video/image processing module in smart glasses in accordance with the present disclosure.

FIG. 6 is a block diagram of one implementation of the video/image processing module 522 in FIG. 5. In the illustrated implementation, the video/image processing module 522 includes a video/image receiving module 602, a video/image analyzing module 604, a video/image stabilization module 606, a pattern recognition module 608, and a video/image display module 610.

The video/image receiving module 602 includes hardware, software, and/or firmware for extracting and receiving image/video data from one or more sources. In some implementations, the video/image receiving module 602 receives the image/video data from the camera(s) 302. The video/image receiving module 602 may determine an operating status of the camera(s) 302 (e.g., on/off) and require the image/video data from the camera(s) 302 accordingly. Or the camera(s) 302 may transmit the image/video data to the video/image receiving module 602 on demand or once it captures the data. In other implementations, the video/image receiving module 602 extracts the image/video data from media data received from the server 412 and/or the user device 416. The media data may include text, image, audio, video data.

In some implementations, the video/image receiving module 602 also identifies the metadata of the received image/video data and transmits the metadata along with the image/video data to the video/image analyzing module 604. The metadata includes, but is not limited, an identifier of a device from which the image/video data was sent, a location of the device, one or more receiving time (e.g., a start time and a stop time of receiving the video data, a time duration), a resolution of an image, etc.

The video/image analyzing module 604 includes hardware, software, and/or firmware for performing an initial analysis of the received video/image data in real time. In some implementations, the video/image analyzing module 604 may classify the video/image data into different groups based on the associated metadata. For example, the video/image analyzing module 604 may extract video/image metadata associated with a specific device from the received data, and determine that the extracted data was from a first user, and place the extracted data in a first group. The video/image analyzing module 604 may also prioritize and queue the data in different groups so that the data can be for further recognition and display at different time slots. For example, responsive to determining that the data in a first group was from a remote presenter of a seminar, the video/image analyzing module 604 sends the first group of data with a high priority to corresponding module(s) to process and display data in real time. However, if a second group of data is from students asking questions, the video/image analyzing module 604 may set a low priority to the data and delay the transmission of the data so that it can be processed and displayed during a Q&A session at the end of a seminar. In some implementations, the video/image analyzing module 604n outputs the data to at least one of the video/image stabilization module 606, the video/image display module 610, and the video/image recognition module 702 for further processing.

The video/image stabilization module 606 includes hardware, software, and/or firmware for performing stabilization on an image/video. The stabilization reduces blurring associated with the motion of a camera (e.g., the camera(s) 302) or other image capture device during exposure. In some implementations, the video/image stabilization module 606 achieves stabilization through implementing an optical image☐stabilization (OIS) function or in☐body image☐stabilization (IBIS) function. The optical image stabilization (OIS) function is based on the lens design of the camera, while the in☐body image☐stabilization (IBIS) function is achieved by moving an actual sensor as the final element in the optical path.

The pattern recognition module 608 includes hardware, software, and/or firmware for automated recognition of patterns and regularities in the received data, which will be described in detail with reference to FIG. 7.

The video/image display module 610 includes hardware, software, and/or firmware for displaying images in two-dimension or three-dimension to the wearer of the smart glasses 100. In some implementations, the video/image display module 610 supports on☐screen notification. A front☐desk of a dental office may send a notification to the smart glasses 100. The video/image display module 610 then displays the received notification at a specific position of the display (e.g., a corner) for a dentist/hygienist wearing the smart glasses 100 to check without interrupting what he/she is working on. This feature is particularly useful for a modern busy dental office. Using this feature, the video/image display module 610 would timely report the dentist notifications such as "Next Patient Arrival, Hygiene Patient ready for Exam," or notes taken by staff when a patient called regarding a specific pain/discomfort, which speeds up the appointment process, avoids the dentist to repeat same questions, and avoids the patient to reiterate her/his visit reason.

In some implementations, the video/image display module 610 may include an overlay generating module 612. In some implementations, the overlay generating module 612 communicates with the other components of the image processing module 522 and/or the recognition module 524 to identify the virtual object image to be presented as an overlay, determine a position of the overlay, and overlay the identified virtual object image at the determined position directly or as picture-in-picture video. For example, when a first dentist wearing the smart glasses 100 is examining an X-ray of a patient, a second dentist sends a comment about the X-ray through the user device 416. The overlay generating module 612 allows the comment to be overlaid on the X-ray for display to the first dentist. The overlay generating module 612 may display the overlay on a built-in output device 510 of the smart glasses 100 and/or on an external output device.

Figure 7:
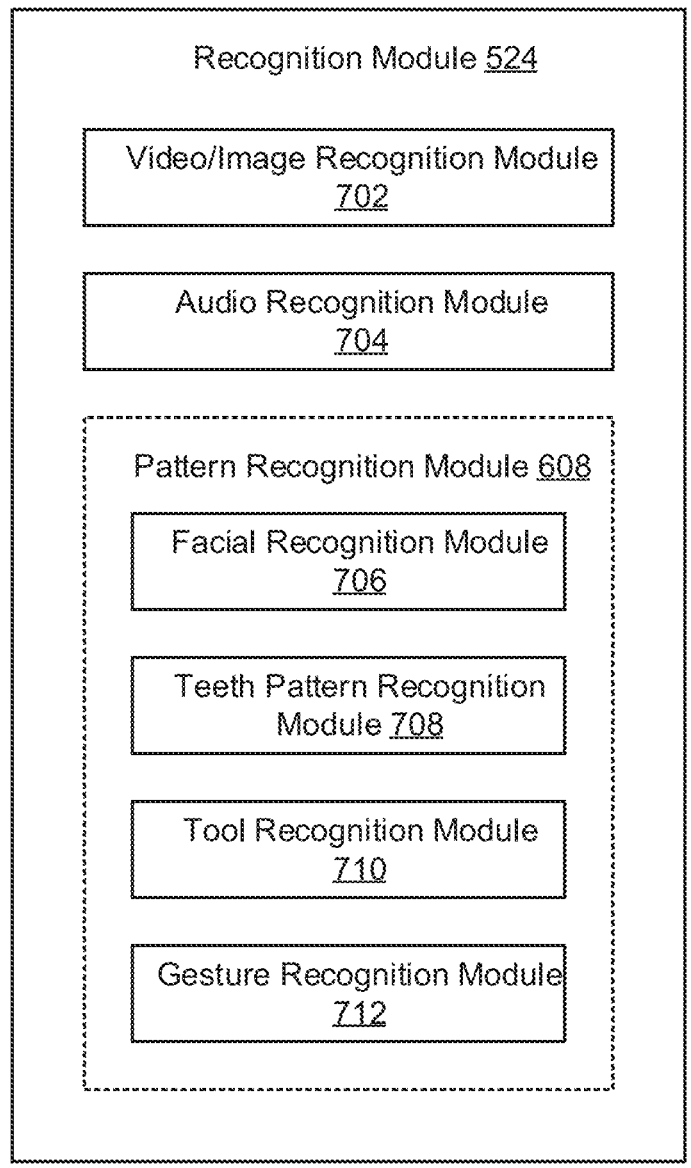
FIG. 7 is a block diagram of one implementation of a recognition module in smart glasses in accordance with the present disclosure.

FIG. 7 is a block diagram of one implementation of the recognition module 524 in FIG. 5. In the illustrated implementation, the recognition module 524 includes a video/image recognition module 702, an audio recognition module 704, and the pattern recognition module 608.

The video/image recognition module 702 includes hardware, software, and/or firmware for detecting, classifying, and recognizing object(s) from the image and video using artificial intelligence (AI) technique or other existing technologies. Since a video is a sequence of images, video recognition is based on image recognition. For simplicity, the below description of the video/image recognition module 702 will mainly focus on image recognition.

In some implementations, the video/image recognition module 702 first processes an image and detects objects in it. For example, the video/image recognition module 702 determines whether an image includes a person or an object, identifies the number of objects/people in the image, and locates each of the objects/people. The video/image recognition module 702 then labels the objects in the image and sorts the objects by certain categories. In some implementations, the video/image recognition module 702 uses at least one image classification model to categorize the image. The image classification model may be an AI model such as a neural network model. For example, the video/image recognition module 702 may build multiple convolutional neural network (CNN) layers and use a CNN model to analyze and classify an image in a category. The video/image recognition module 702 may identify a specific object based on the classification. For example, the video/image recognition module 702 recognizes a specific tooth based on the first category of the position of the tooth and a second category of the cracked condition of the tooth. The video/image recognition module 702 may further analyze the detected objects. For instance, the video/image recognition module 702 may further analyze the identified teeth from an X-ray image, and automatically identify cavities, cracked teeth, broken teeth, or other items not visibly apparent, etc. Once the video or image recognition is complete, the video/image recognition module 702 communicates with the video/image processing module 522 and the information delivery and display mechanism 528 to display the recognition result on the smart glasses 100 for viewing by the glasses wearer.

The audio recognition module 704 includes hardware, software, and/or firmware for performing audio recognition to interpret an audio input and generate an output. The audio input may come from a user or from other sources in the environment where the smart glasses 100 are used by the user. The output may be an instruction for performing an action. For example, based on the output of the audio recognition module, a headlamp 304 may be turned off, the recording of a video may be paused. The audio recognition module 704 generates a variety of instructions for "hands-free" operations, which is particularly advantageous in the medical field because cross-contamination can be prevented with "hands-free" operations.

Audio recognition is of particular importance in the present disclosure because an audio input may be used to generate a voice command to control a specific element of the smart glasses 100, or it may merely be part of a conversation among users and should not be used to generate an audio output. One challenge of the audio recognition module 704 is to distinguish a voice command from non-command audio resources among multiple audio inputs.

In some implementations, the audio recognition module 704 extracts one or more audio signals from the received media data. The media data includes various types of data such as text, image, video, and audio data. The audio recognition module 704 identifies the source of each audio signal, which achieves a first level of differentiation between the voice command and non-command. For example, if the audio recognition module 704 determines that an audio input is the glasses wearer's voice, this audio input could be a command for glasses operation. The audio recognition module 704 also recognizes the content of the audio input to help achieve a second level of differentiation. Therefore, if the audio recognition module 704 recognizes that the glasses wearer says "turn off the camera," it is very likely that the glasses wearer means to stop the operation of the camera(s) 302 of the smart glasses 100. However, it could also be that the glasses wearer just mentioned "turn off the camera" in a discussion with another user. Although the wording sounds like a voice command, this audio input is just a part of the conversation. In this regard, the audio recognition module 704 may analyze the context surrounding the audio input to determine whether it is a voice command or non-command, which achieves a third level of differentiation. For example, if the audio recognition module 704 parses a likely-command from the audio input, it would examine the preceding and succeeding audio data to determine whether this likely-command is really a voice command. The audio recognition module 704, therefore, ensures the accurate glasses operation while maintaining smooth conversations among users based on this three-level differentiation mechanism.

The pattern recognition module 608 uses one or more machine learning algorithms to automatically, accurately, and efficiently identify patterns and objects. For example, the pattern recognition module 608 recognizes patterns by identifying representation data (i.e., actual data) of a pattern and matching the identified data to statistical data extracted from the pattern that defines the pattern (i.e., stored data) to determine a data classification, i.e., whether the actual data represents a pattern. In some implementations, the pattern recognition module 608 generates and outputs a recognition result. The pattern recognition module 608 may transmit the recognition result to a corresponding module for further processing or store the recognition result in a built-in micro SD card of the smart glasses 100 or in the data store 414 of the server 412 for future use.

In some implementations, the pattern recognition module 608 includes a facial recognition module 706, a teeth pattern recognition module 708, a tool recognition module 710, and a gesture recognition module 712.

The facial recognition module 706 is responsible for recognizing a human face and generating a recognition result. In some implementations, the facial recognition module 706 identifies facial features from a portrait image or a video of a client based on biometric data, and compares the identified facial features with the stored facial features of known faces based on one or more AI models. The portrait image may be an optimized image captured by the camera(s) 302. If a match is found, the facial recognition module 706 recognizes the face by associating this face to an identity of a particular human. For example, the facial recognition module 706 may perform facial recognition on a still image or an image extracted from a video to identify a patient in order to help retrieval of the appropriate patient medical record.

In dentistry, the facial recognition module 706 allows a dentist/hygienist who wears the smart glasses 100 to automatically detect which patient the dentist/hygienist is working on, and automatically record and store images, videos and/or other information related to the patient to an appropriate patient file (e.g., a patient profile). In addition, the facial recognition module 706 may instruct the video/image display module 610 to overlay certain alerts/notes at a particular position of a screen or projection. In some implementations, the facial recognition module 706 may also cooperate with the element control module 526 to configure the viewer access rights (e.g., an alert is only visible to a specific dentist/hygienist) and to configure other display preferences (e.g., the alert is shown on a screen corner to avoid interruption to routine tasks). The facial recognition module 706 may further classify the alerts/notes and arrange the classified alerts/notes to be displayed at different positions or with different colors to visually remind the dentist/hygienist of different priorities/importance, which will be especially helpful for the dentist/hygienist to provide better and proper care to a patient. The medical alerts/notes may include a reminder of allergies to certain dental anesthetic compounds or latex allergies, a reminder that a patient has a high level of dental anxiety, a preference related to hand scaling or ultrasonic scaling, or useful information about last appointment date and treatment rendered, etc.

The teeth pattern recognition module 708 is responsible for recognizing a pattern/condition of a tooth and generating a recognition result. For example, the teeth pattern recognition module 708 may identify a pattern of a tooth based on features including color, cavity, fillings, etc. The recognition result may include a classification of the tooth based on the identified pattern such as healthy, problematic, level 1 problem, etc. The teeth pattern recognition module 708 may also generate a recognition result including a recommended treatment determined based on the pattern and classification of a tooth. In some implementations, based on the recommended treatment, the smart glasses may automatically adjust certain components (e.g., light source, view angles, etc.) accordingly to prepare for a recommended treatment.

The tool recognition module 710 is responsible for recognizing a tool and generating a recognition result. The tool recognition module 710 may identify a specific tool that a dentist is using at a specific time when operating on a patient. The tool recognition module 710 may notify the element control module 526 to adjust the glasses settings to adapt to the use of the specific tool by a specific user, thereby automatically and dynamically optimizing the use of the smart glasses 100 with reduced, or without, manual intervention/input. In this way, the applicability and efficiency of the smart glasses 100 are improved. In some implementations, the tool recognition module 710 may also feed back the recognition result including the glasses settings adjustment associated with a specific tool and a specific glasses wearer into an AI model such that the AI model may be trained and refined to provide more customized and accurate glasses settings adjustment, which further increases the applicability and efficiency of the smart glasses 100.

The gesture recognition module 712 is responsible for recognizing gestures from a glasses wearer and generating a recognition result. In some implementations, the gesture recognition module 712 interprets human gestures via a machine learning algorithm and outputs an operation command/instruction based on the gesture interpretation. For example, the gesture recognition module 712 may determine that the glasses wearer moves his eyes to a certain direction and notify the element control module 526 to move the camera(s) 302 towards that direction. A gesture command supplements a voice command and/or a foot-pedal command to further facilitate the operation of the smart glasses 100.

Figure 8:
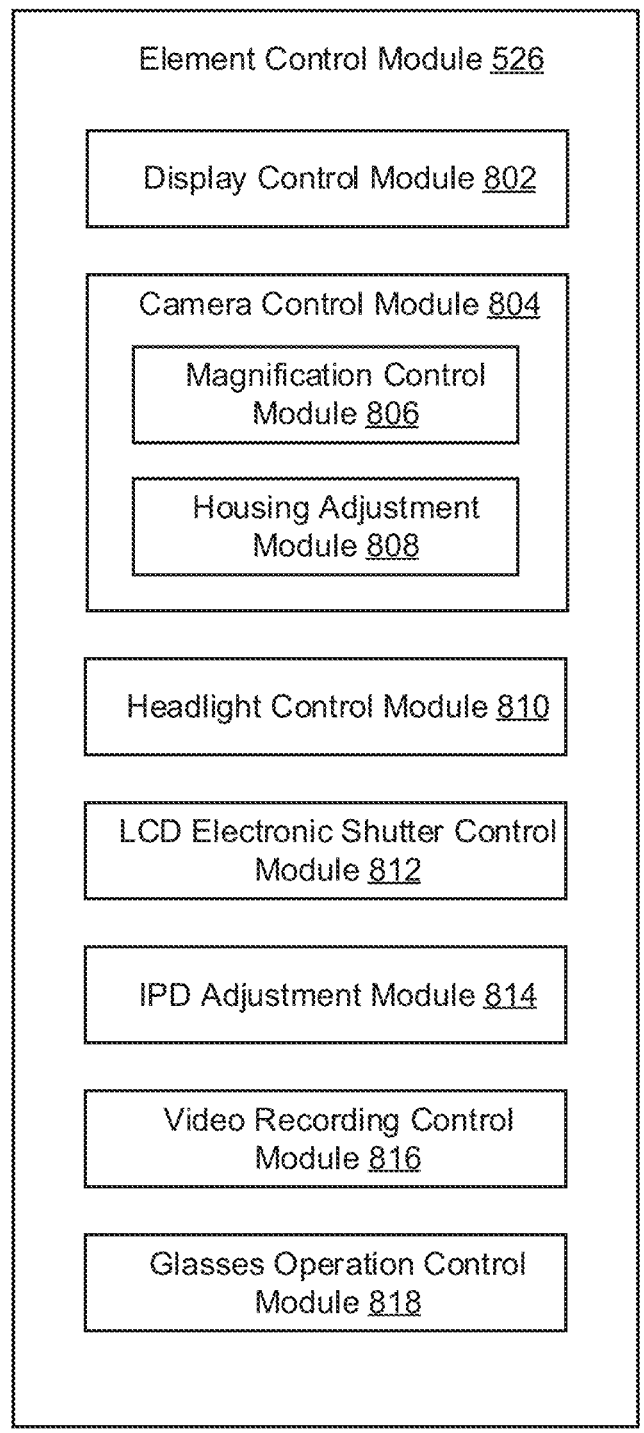
FIG. 8 is a block diagram of one implementation of an element control module in smart glasses in accordance with the present disclosure.

FIG. 8 is a block diagram of one implementation of the element control module 526 in FIG. 5. The element control module 526 allows elements of the smart glasses 100 to be controlled or adjusted based on user-specific settings of a glasses wearer and based on requirements of a specific operation. Suppose multiple part-time dental hygienists in a dental office share a pair of smart glasses as they work different days. A first hygienist and a second hygienist may find that the camera(s) 302, when initiated, is in a different magnification because of the different settings customized to each individual hygienist. Also, a hygienist may find that the camera(s) 302 is in a different magnification because it is initiated by a different operation. In some implementations, the element control module 526 controls the elements of the smart glasses 100 via voice control or foot-pedal control, and sometimes via gesture control.

In some implementations, the element control module 526 takes user manual input or system default configuration as initial user-specific settings. The elemental control module 526 may then collect element adjustments during user operations and modify the initial user-specific settings based on the collected adjustments. In some implementations, the element control module 526 cooperates with a model engine (not shown) to perform machine learning on the collected element adjustments and refine the user-specific settings.

In the illustrated implementation, the element control module 526 includes a display control module 802, a camera control module 804, a headlight control module 810, an LCD electronic shutter control module 812, an inter-pupillary distance (IPD) adjustment module 814, a video recording control module 816, and a glasses operation control module 818.

The display control module 802 includes hardware, software, and/or firmware for specifying display parameters/settings (e.g., image size, resolution, etc.) of smart glasses 100 based on user-specific requests. For example, the display control module 802 may determine the size of an overlay and a position of an overlay for a specific user. The display control module 802 may determine the position of an overlay based on the type of image/video data included in the overlay such as overlaying top-priority alert in the center of a screen. The display control module 802 may also update the display parameters based on an update of the user settings.

The camera control module 804 includes hardware, software, and/or firmware for turning on/off the camera(s) 302 and specifying and adjusting the camera preferences. The camera control module 804 may control the operation status of the camera (on/off) and other preferences via voice, foot-pedal, or even gesture. In some implementations, the camera control module 804 includes a magnification control module 806 and a housing adjustment module 808.

The magnification control module 806 controls the zoom/magnification of camera(s) 302 of the smart glasses 100. The camera(s) 302 is equipped with a front element lens group that is capable of providing at least a 3× optical zoom. Additionally, the camera(s) 302 also supports sufficient resolution to allow at least a 10× digital zoom. The combination of optical zoom and digital zoom would result in a multiplied factor of virtual zoom/magnification.

Responsive to a voice command or a foot-pedal command from the glasses wearer, the magnification control module 806 may change the focal length of the camera(s) 302 to vary the magnification of the operating field of the wearer of the smart glasses 100. This is especially advantageous when a user working on small objects and confined spacing needs to magnify the field of view. The smart glasses 100 therefore can be used to replace existing optical magnifying glasses currently used by many dentists, hygienists, surgeons, etc.

The housing adjustment module 808 controls the adjustment of the housing of the camera(s) 302, for example, the angle and tilt of the camera to fit the needs of the operating user.

The headlight control module 810 includes hardware, software, and/or firmware for controlling the illumination of an operating field through the light source 304 equipped with the smart glasses 100. In dental operations, the light source 304 usually includes two LED headlamps. One would transmit white light, while the other transmits amber☐colored light. The amber LED is used to significantly increase the working time when working with light☐sensitive composite resin restorative materials. In some implementations, the LED headlamps 304 and the camera(s) 302 share one physical enclosure/housing, which is mounted on a hinge 108 near the midline/bridge of the smart glasses 100. Responsive to receiving a voice command or a foot-pedal command from a user, the housing adjustment module 808 and the headlight control module 810 control the hinge mount to tilt and adjust the angle of the enclosure/housing so that the camera(s) 302 may face in one direction (e.g., downward) while the user's head position remains in another direction (e.g., upright). This ergonomic design of the smart glasses 100 improves posture and reduces neck strain of the wearer of the smart glasses 100 while he/she is working on patients.

The LCD electronic shutter control module 812 includes hardware, software, and/or firmware for adjusting an LCD electronic shutter to change the image quality. In some implementations, an LCD electronic shutter is placed right behind each prism of the smart glasses 100. The LCD electronic shutter control module 812 changes the translucency or opacity of the LCD electronic shutters to provide a darker or brighter background to change the image contrast/projection for different viewing effects. For example, when the smart glasses 100 are off/non-operational, the LCD electronic shutter control module 812 allows the LCD electronic shutters as well as the prisms to be transparent so that the glasses wearer may see an object clearly without any obstruction or distortion.

The IPD adjustment module 814 includes hardware, software, and/or firmware for adjusting the lens element of the smart glasses 100 to adapt to the inter-pupillary distance of individual users. This design feature of personal customization to individual inter-pupillary distance allows mass production with in-the-field customization, which will be significantly different from the existing practice in which a trained technician needs to go and measure the inter-pupillary distance of each user.

In a scenario where multiple part-time dental hygienists share a pair of smart glasses 100, multiple elements of the smart glasses 100 may be adjusted to accommodate the preferences of the individual users and application needs. Upon receiving a voice command or foot-pedal command from each hygienist, the IPD adjustment module 814 may change the IPD of the glasses and the camera control module 804 may change the angle and magnification of the camera(s) 302 so that the smart glasses 100 can function optimally for each hygienist. Different modules included in the element control module 526 adjust elements of glasses based on user-specific settings. A user may manually input the user-specific settings. Each module responsible for certain element control may dynamically and automatically update and store the user-specific settings based on the machine learning from the progressive usage of the smart glasses 100 by each user. For example, a first hygienist prefers 2× magnification, a 45-degree camera angle from horizontal, and an IPD of 55 mm, a second hygienist prefers 3× magnification, a 30-degree camera angle from horizontal, and an IPD of 65 mm, while a third hygienist has a preference of entirely different set of parameters. As various hygienists rotate throughout workdays and share the smart glasses 100, each glasses wearer can easily and quickly adjust the smart glasses to a customized operation state via the camera control module 804, the IPD adjustment module 814, and other modules once the wearer selects/recalls the stored preferences via voice control or foot-pedal control. Alternatively, by providing a voice command announcing the identity of a wearer of the smart glasses 100, the preferred settings for that wearer may be automatically adjusted.

The video recording control module 816 includes hardware, software, and/or firmware for determining whether and how to record the image/video data for documentation purposes. For example, if a dentist wearing the smart glasses 100 initiates a recording process with voice command or foot-pedal control, the video recording control module 816 may communicate with the camera control module 804 to set the camera(s) 302 to a recording mode (e.g., constantly record), and upload and store the recorded video data to a local or cloud□based server including the server 412. At a later date, if a dental insurance attempts to deny any claims of procedures that the dentist rendered, the video recording control module 816 may retrieve the stored video responsive to a request from the dentist. The dentist can then use the video for a demonstration. Or if an unscrupulous patient accuses the dentist of damaging an adjacent tooth, the dentist can defend himself using the video evidence. The video recording control module 816, therefore, helps the dentist activate a video recording with a simple voice command or foot-pedal control.

The glasses operation control module 818 includes hardware, software, and/or firmware for controlling different types of glasses operations. For example, the glasses operation control module 818 may communicate with the power source 514, output device 510, and other components of the smart glasses 100 to power on/off the smart glasses 100, to start/stop data transmission between the smart glasses 100 and user device 416 or the server 412, to swap batteries of the smart glasses 100, etc., via voice or foot-pedal control.

It is to be noted that various modules described in FIGS. 6-8 are merely for illustrative purposes, but not to limit the functions of the disclosed smart glasses 100. A person skilled in the art may appreciate that the disclosed smart glasses 100 may contain fewer components or more components as illustrated in FIGS. 6-8 without derivation form the principle and spirit of the present disclosure.

Figure 9:
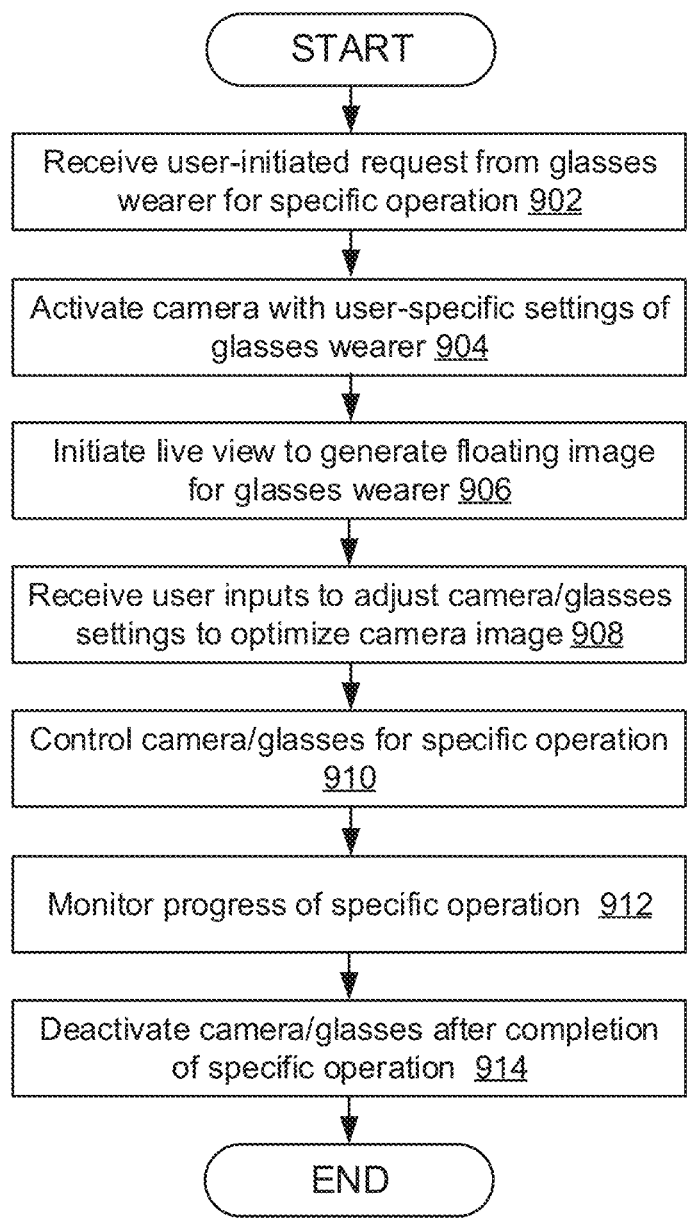
FIG. 9 is a flowchart of an example method for using smart glasses in accordance with the present disclosure.

FIG. 9 is a flowchart of an example general method 900 for using a pair of smart glasses 100. The smart glasses 100 include a control unit 406*a* and a camera(s) 302. At step 902, the smart glasses 100 receive a user-initiated request from a wearer of the smart glasses 100 for a specific operation. For example, the smart glasses 100 receive a voice request for conducting a general oral exam for a patient. At step 904, the control unit 406*a* of the smart glasses 100 activates the camera(s) 302 with user-specific settings of the wearer of the smart glasses 100. For example, the control unit 406*a* may turn on the camera(s) 302, and adjust the magnification of the camera(s) 302 based on stored user-preferred settings and/or the requirements of the general oral exam. At step 906, the smart glasses 100 initiate live view to generate a floating image for the wearer of the smart glasses 100. For example, the control unit 406*a* places the camera(s) 302 in a constantly recording state and streamlines the recorded video for live viewing by the dentist. If the dentist also retrieves image(s) of the patient's previous oral exam, the control unit 406 may generate a floating image of the previous oral exam overlaid on the image of the current oral exam so that the dentist may make an accurate diagnosis based on the comparison.

At step 908, the control unit 406*a* of the smart glasses 100 receives user inputs to adjust camera settings to optimize the camera image, for example, changing the magnification of the camera(s) 302 for better image quality. At step 910, the control unit 406*a* automatically controls the camera(s)/glasses for the specific operation responsive to inputs. For example, the control unit 406*a* may change the color of headlamps 304 as the specific operation moves to a specific step. The control unit 406*a* monitors the progress of the specific operation at step 912 and deactivates the camera after completion of the specific operation at step 914. For example, the control unit 406*a* terminates the operation of the camera(s) 302 responsive to receiving a completion command from the dentist or if the control unit 406*a* does not receive a command from the dentist for a certain period of time (e.g., 3 minutes, 5 minutes, 10 minutes, 20 minutes, etc.). It should be noted that the user input involved in operating the smart glasses 100 could be a command from voice, foot-pedal, or gesture of the wearer of the smart glasses 100.

Figure 10:
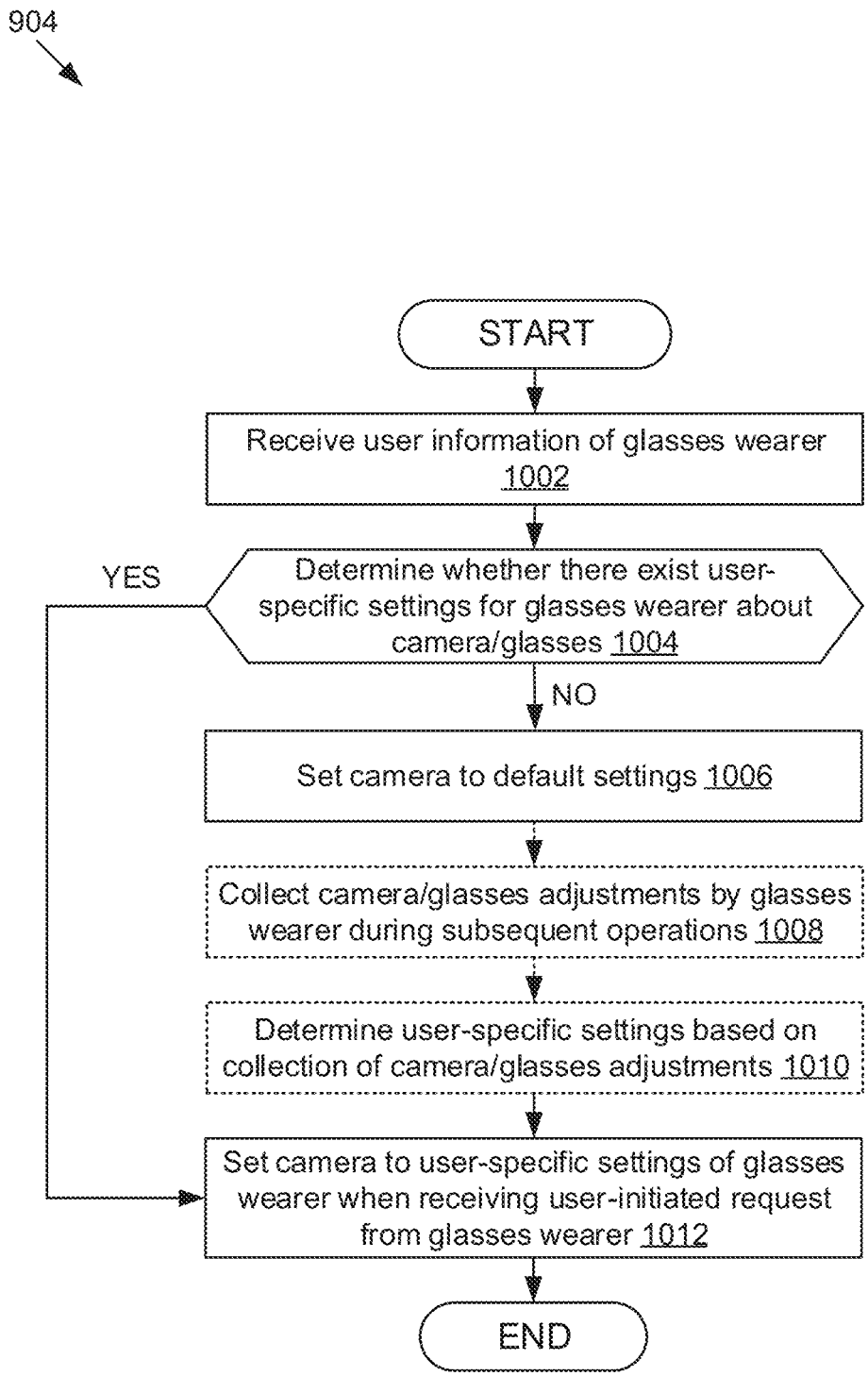
FIG. 10 is a flowchart of an example method for specifying user settings for the smart glasses.

FIG. 10 is a flowchart of an example method 904 for specifying user settings for the smart glasses 100. This method corresponds to step 904 in FIG. 9. The smart glasses 100 include the element control module 526 and the camera(s) 302. At step 1002, the element control module 526 receives user information of a wearer of the smart glasses 100. At step 1004, the element control module 526 determines whether there exist user-specific settings for the glasses wearer about the camera(s)/glasses based on the user information of the wearer of the smart glasses 100. If user-specific settings exist, the method 904 moves to step 1012 to set the camera(s) 302 to user-specific settings of the glasses wearer when receiving a user-initiated request from the wearer of the smart glasses 100.

However, if there are no user specific settings, the element control module 526 sets the camera(s) 302 to default settings at step 1006. In other words, the element control module 526 takes user manual input or system default configuration as initial user-specific settings. At step 1008, the element control module 526 collects camera/glasses adjustments by the wearer of the smart glasses 100 during subsequent operations. At step 1010, the element control module 526 determines user-specific settings based on a collection of camera/glasses adjustments. In some implementations, the element control module 526 cooperates with a model engine (not shown) to perform machine learning on the collected adjustments and refine the user-specific settings. Once the refined/modified user-specific settings are determined, the element control module 526 then moves to step 1012 to set the camera to the modified/updated user-specific settings of the glasses wearer responsive to receiving a user-initiated request from the wearer of the smart glasses 100.

Figure 11:
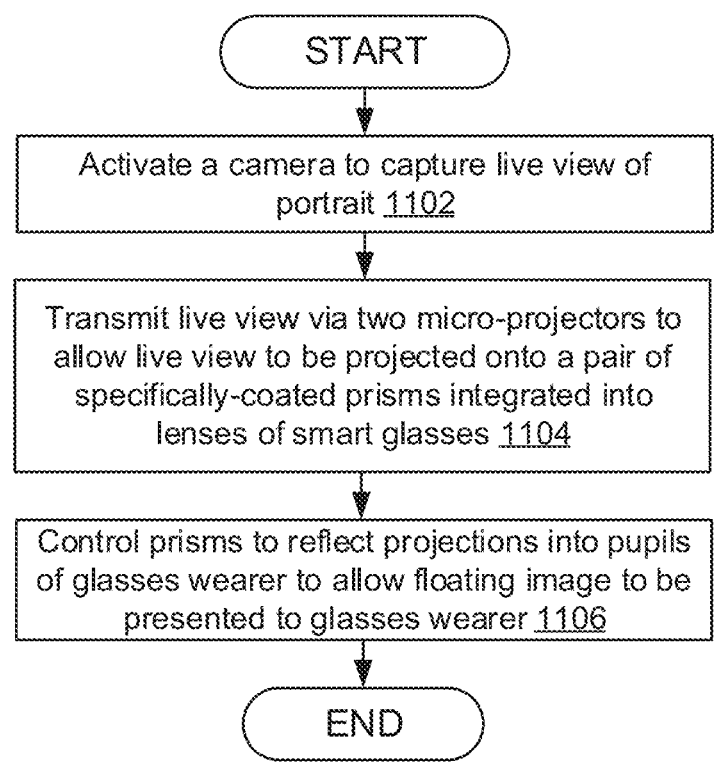
FIG. 11 is a flowchart of an example method for creating a floating image in accordance with the present disclosure.

FIG. 11 is a flowchart of an example method 906 for creating a floating image. This method corresponds to step 906 in FIG. 9. At step 1102, the smart glasses 100 activate a camera 302 to capture a live view of a portrait. For example, the smart glasses 100 turn on the camera(s) 302 to obtain a live view of a patient's portrait responsive to receiving a request for performing a tooth filing for the patient from a dentist. The request may be a voice command. At step 1104, the smart glasses 100 transmit the live view via two micro-projectors to allow the live view to be projected onto a pair of specifically-coated prisms integrated into lenses of the smart glasses 100. At step 1106, the smart glasses 100 control the prisms to reflect projections into pupils of a glasses wearer to allow a floating image to be presented to the wearer (e.g., the dentist) of the smart glasses 100.

Figure 12:
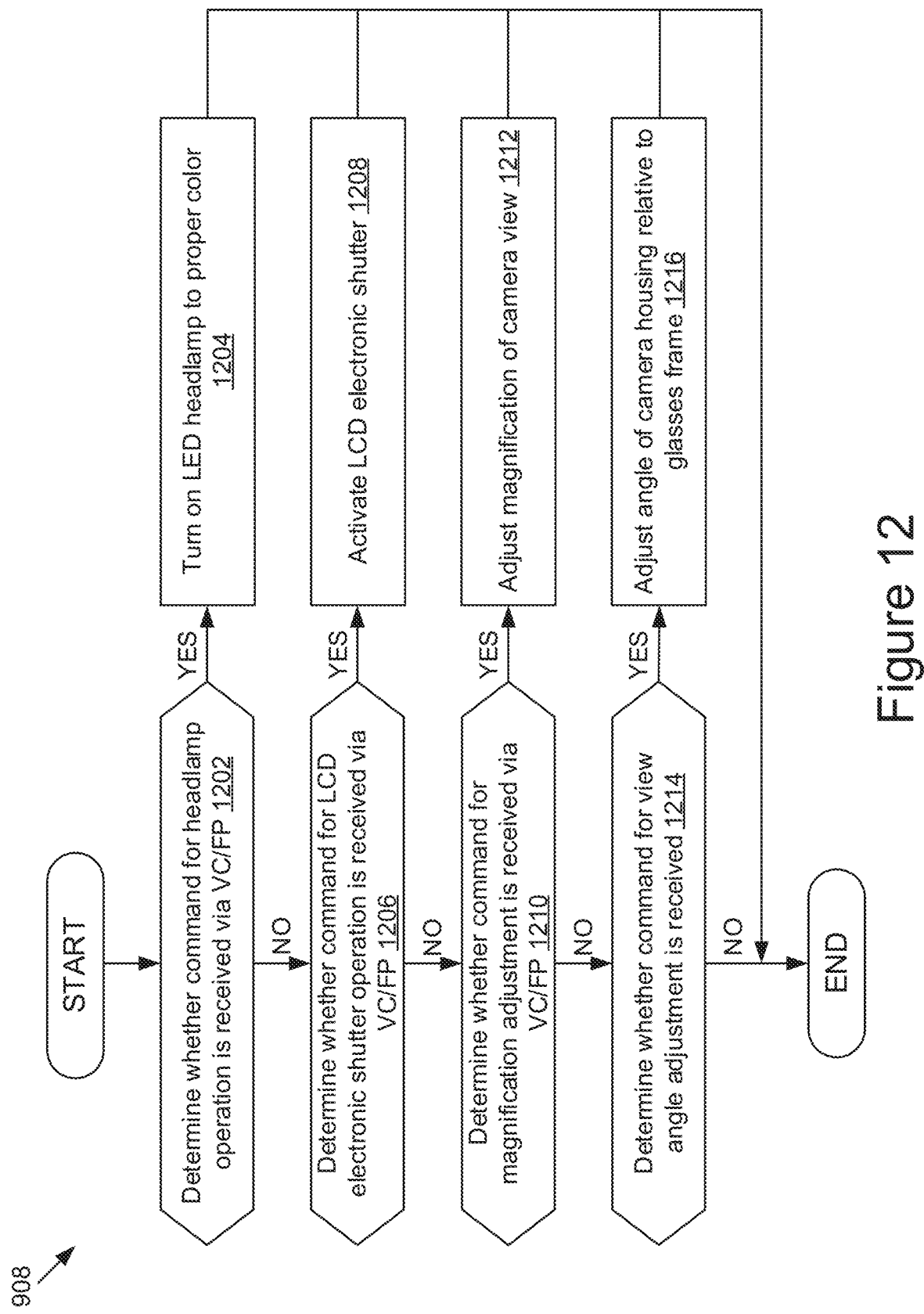
FIG. 12 is a flowchart of an example method for performing camera/glasses adjustment in accordance with the present disclosure.

FIG. 12 is a flowchart of an example method 908 for performing camera/glasses adjustment. This method corresponds to step 908 in FIG. 9. At step 1202, the element control module 526 determines whether a command for headlamp operation is received via voice or foot-pedal control (VC/FP). If yes, at step 1204, the element control module 526 turns on a LED headlamp 304 to a proper color. For example, the element control module 526 may switch light color between white and amber in dental operations. If there is no command for headlamp operation, at step 1206, the element control module 526 determines whether a command for LCD electronic shutter operation is received via VC/FP. If yes, at step 1208, the element control module 526 activates the LCD electronic shutter. For example, the element control module 526 changes the translucency or opacity of the LCD electronic shutters to provide a darker or brighter background to change the image contrast/projection for different viewing effects. However, if there is no command for LCD electronic shutter operation, at step 1210, the element control module 526 determines whether a command for magnification adjustment is received via VC/FP. If yes, at step 1212, the element control module 526 adjusts the magnification of the camera view. For example, the element control module 526 may change the focal length of the camera(s) 302 to vary the magnification of an operating field of a wearer of the smart glasses 100. If there is no command for magnification adjustment, at step 1214, the element control module 526 determines whether a command for view angle adjustment is received. If yes, at step 1216, the element control module 526 adjusts the angle of camera housing relative to the glasses frame. Otherwise, the method corresponds to step 908 ends.

Figure 13:
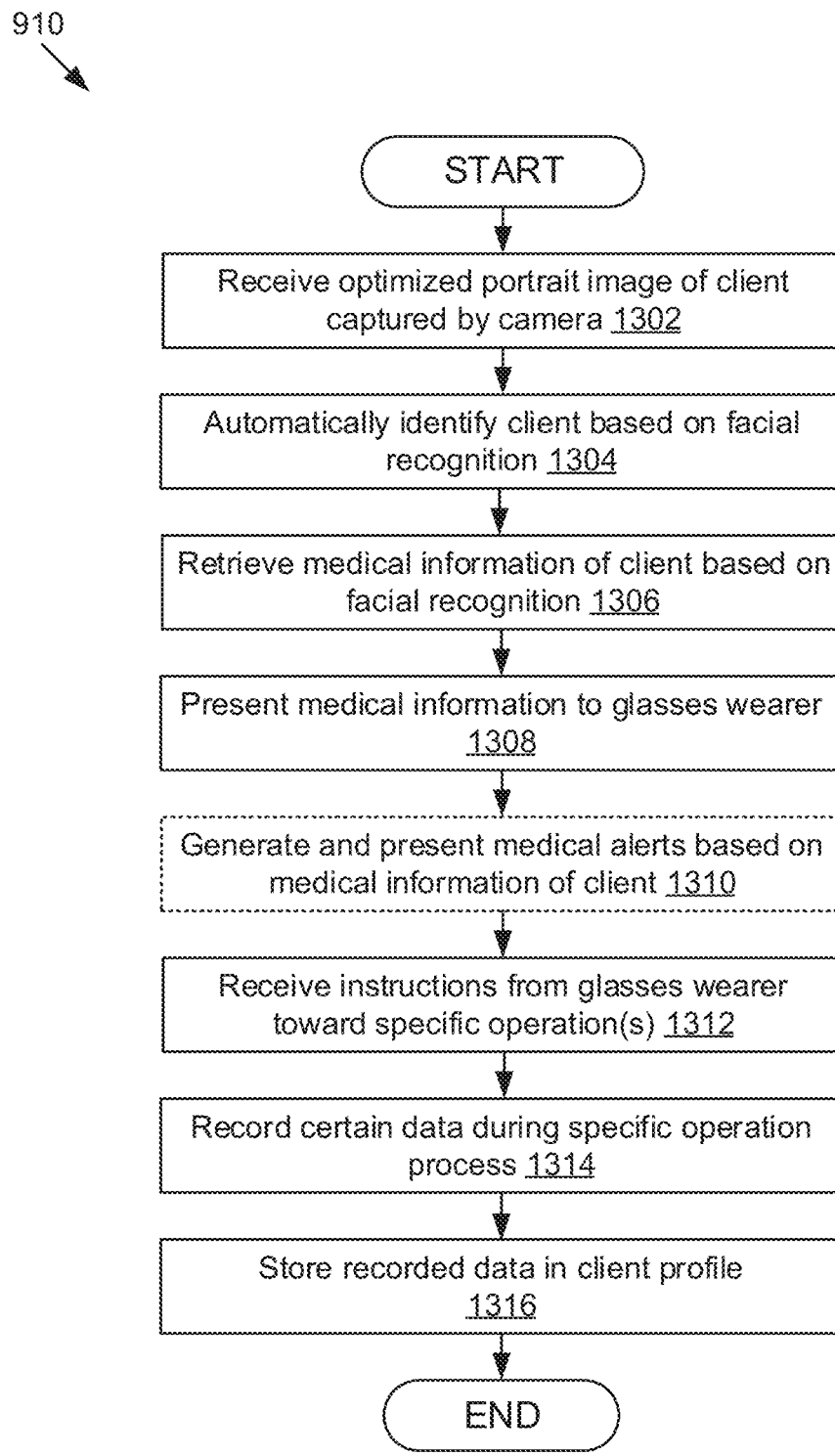
FIG. 13 is a flowchart of an example method for controlling camera/glasses for a specific operation in accordance with the present disclosure.

FIG. 13 is a flowchart of an example method 910 for controlling camera/glasses for a specific operation(s). This method corresponds to step 910 in FIG. 9. At step 1302, the smart glasses 100 receive an optimized portrait image of a client (e.g., the patient) captured by the camera(s) 302. At step 1304, the smart glasses 100 automatically identify the client based on facial recognition. For example, the smart glasses 100 identifies facial features from the portrait image and compares the identified facial features with stored facial features of known faces based on one or more AI models. At step 1306, the smart glasses 100 retrieve medical information of the client based on facial recognition, i.e., the smart glasses 100 can retrieve specific information of a specific client once the identity of the client becomes available.

At step 1308, the smart glasses 100 present the medical information to a wearer (e.g., a doctor) of the smart glasses 100. Under certain circumstances, the smart glasses 100 also generates and presents medical alerts based on the medical information of the client at step 1310. For example, the medical alerts may be a reminder that the patient needs to visit the doctor before a certain date, a reminder that the patient is allergic to certain dental anesthetic compounds, a reminder that the patient needs x-ray, etc. In some implementations, the next actions following the medical alerts may be also performed automatically. For instance, a message for scheduling the next visit before the certain date may be automatically sent to a front desk, and/or a message for X-ray instruction may be automatically sent to an examination specialist with or without the dentist's confirmation via voice command. At step 1312, the smart glasses 100 receive instructions from the glasses wearer toward specific operation(s), for example, remote assistance application, multiple patient communications, etc. At step 1314, the smart glasses 100 record certain data during a specific operation process. At step 1316, the smart glasses 100 stores the recorded data in a client profile.

FIGS. 14A-D are flowcharts of an example method for implementing specific operations responsive to receiving instruction from a wearer of the smart glasses 100. These flowcharts labelled as 1312a-1312d correspond to step 1312 in FIG. 13.

Figure 14A:
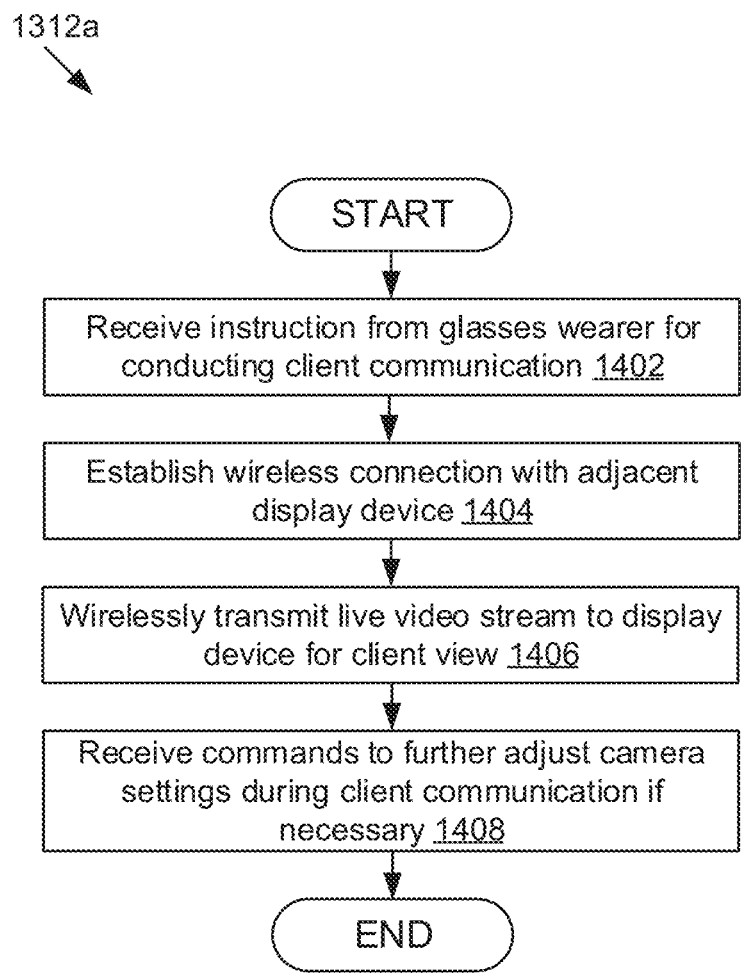
FIGS. 14A-D are flowcharts of example methods for implementing specific operations responsive to receiving instructions from a wearer of the smart glasses in accordance with the present disclosure.
Figure 14B:
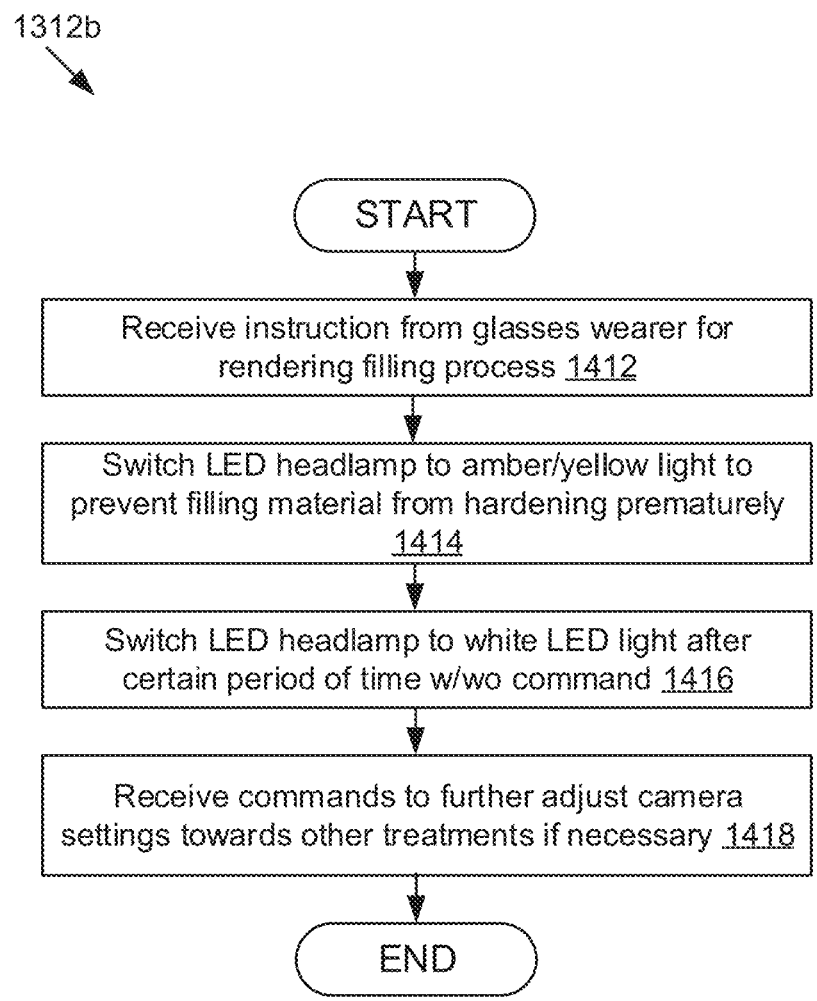

The flowchart 1312a of FIG. 14A illustrates a use case of patient communication. According to the flowchart 1312a of FIG. 14A, at step 1402, the smart glasses receive instruction from the glasses wearer for conducting client communication. At step 1404, the smart glasses 100 establish a wireless connection with an adjacent display device. At step 1412, the smart glasses 100 wirelessly transmit a live video stream to a display device for the client view. At step 1408, the smart glasses 100 receive commands to further adjust camera settings during the client communication if necessary.

In one example scenario, when a new patient presents for a comprehensive exam at a first visit, responsive to voice command(s) (VC) or foot-pedal command(s) (FP) from a dentist wearing the smart glasses 100, the smart glasses 100 may activate and adjust camera housing so that the camera(s) 302 captures the patient's portrait image at a wide angle view. It should be noted that there is no camera magnification in a wide-angle view. The smart glasses 100 either stores the captured image internally to a memory card or transmits the image to a remote server (e.g., server 412) to attach to an electronic file of the patient.

The dentist reviews the patient's medical history and determines to proceed with an intraoral exam. Based on the VC/FP from the dentist about the intraoral exam, the smart glasses 100 adjust the magnification of the camera view to 2.5× and turn on a white LED lamp on top of the camera(s) 302. The smart glasses 100 may also activate a wireless live stream video to an adjacent monitor responsive to the VC/FP from the dentist, so that the patient can see what the dentist is seeing in real□time. If the bright background light in the dentist's office makes it difficult for clearly viewing a projected image, with the VC/FP from the dentist, the smart glasses 100 may activate the LCD electronic shutter to block out the background light to provide a clearer projection. With the VC/FP from the dentist, the smart glasses 100 also examine and capture images or record a video of specific teeth. The smart glasses 100 further store the images and video in a built-in memory card, and additionally transfers the images and video through a Wi□Fi connection to the server 412 for storing in the data store 414.

During the operation of the intraoral exam, the smart glasses 100 may identify an issue, for example, based on pattern recognition. The issue may include decay, crack, failed fillings, poor dental hygiene, etc. If an issue is detected, responsive to receiving the VC/FP from the dentist, the smart glasses 100 may increase the camera magnification from 2.5× to 4×, 8×, or 10× and capture images to document the findings. In the meantime, the smart glasses 100 may transmit the images to an external display device so that the patient can see what the operation is going on in his/her mouth. Also, upon receiving the VC/FP from the dentist, the smart glasses 100 may change magnification as needed, so that the dentist can examine a region or a specific tooth surface without taking his/her hands away from the patient's mouth and without grabbing different tools/devices.

Once the intraoral exam is complete and the VC/FP is received from the dentist, the smart glasses 100 may deactivate the live view camera, LCD electronic shutter, and white LED lamp when the dentist is still wearing the smart glasses 100. There is no need for the dentist to remove the smart glasses 100 because the deactivation of the view camera of the smart glasses 100 would lead the lens of the camera to become clear and transparent and thus would not disrupt the dentist's vision.

The flowchart 1312b of FIG. 14A illustrates a use case of patient treatment. According to the flowchart 1312b of FIG. 14B, at step 1412, the smart glasses 100 receive instruction from the glasses wearer for rendering the filling process. At step 1414, the smart glasses 100 switch a LED headlamp 304 to amber/yellow light to prevent filling material from hardening prematurely. At step 1416, the smart glasses 100 switch the LED headlamp 304 to white LED light after a certain period of time with/without a command. At step 1418, the smart glasses 100 receive commands to further adjust camera settings towards other treatments if necessary.

In an example scenario, a dentist wearing the smart glasses 100 uses the VC/FP to start this treatment rendering process when a patient presents at his/her office for a composite tooth☐colored filling. Upon receiving the VC/FP, the smart glasses 100 activate and adjust the camera(s) 302 and an LCD shutter and also turns on a white LED. The smart glasses 100 also set the camera magnification at 1× to provide a clear view of the injection site and adjacent tissue for landmark reference and to support local anesthetic injection. Once the patient is anesthetized, the dentist begins treatment. With the VC/FP received from the dentist, the smart glasses 100 then change the camera magnification to a range of 2.5×☐10× throughout the procedure so that the dentist can assess decay removal and restore the tooth to proper contours and anatomy.

The smart glasses 100 also allow the dentist to take photos/videos as necessary to document the extent of decay or for shade and anatomy matching based on the dentist's VC/FP. The smart glasses 100 store the images and videos on a memory card and/or transmit the data to the server 412 through a Wi☐Fi connection. The stored images may later be submitted to a dental insurance company as a proof of treatment for insurance claims or if requested by the insurance company, or sent to a dental laboratory to make an esthetic restoration.

Once the dentist has removed the decay and sent a VC/FP, the smart glasses 100 may switch to an amber/yellow LED lamp to start a filling process. It should be noted that dental composite resin material is only activated by white light. Having an amber☐colored light allows the dentist to extend working time without having the filling material harden prematurely. Once the filling is completed, the smart glasses 100 switch back to the white LED light based on the VC/FP from the dentist. The dentist may send VC/FP upon completion of the procedure. With this VC/FP, the smart glasses 100 may take post☐operation photos at various magnifications and angles, and turn off the live view camera and LCD shutter while the dentist is having a normal conversation with the patient about post☐operation care or maintenance with no obstruction to his/her field of view.

Figure 14C:
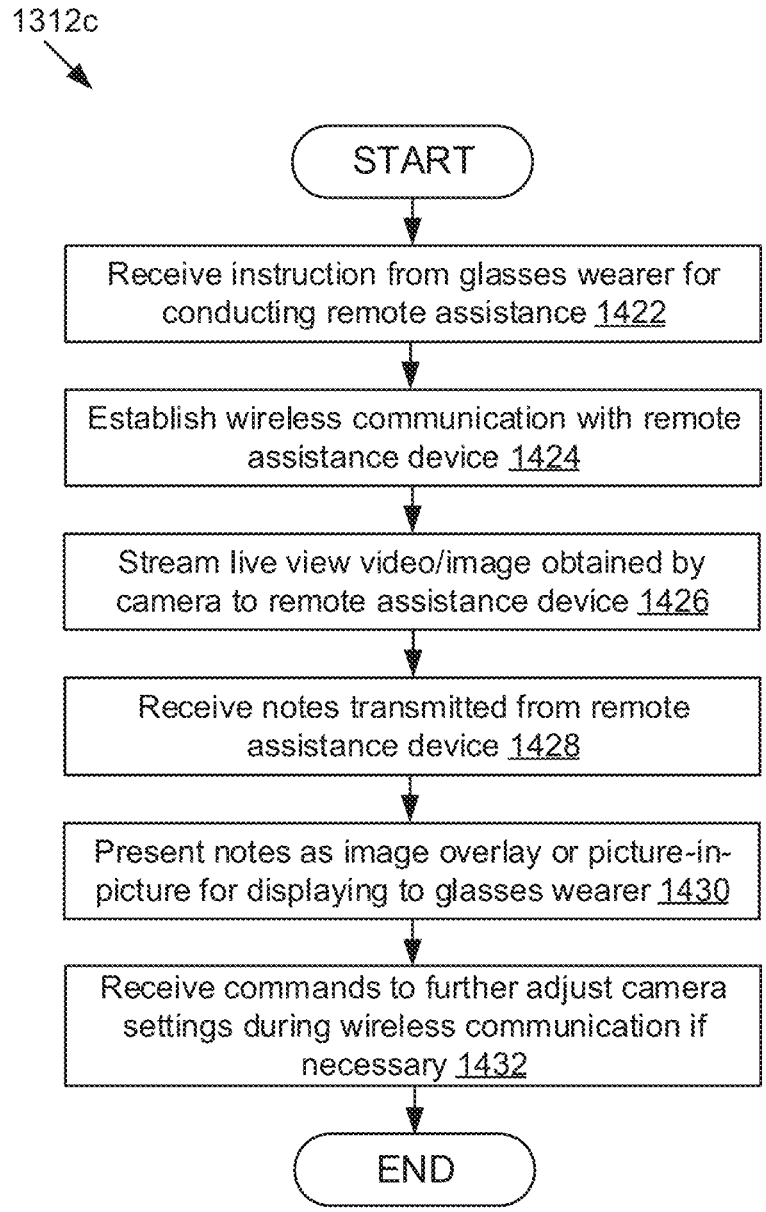

The flowchart 1312c of FIG. 14C illustrates the operation of smart glasses in a remote assistance. According to the flowchart 1312c of FIG. 14C, at step 1422, the smart glasses 100 receive instruction from the glasses wearer for conducting remote assistance. At step 1424, the smart glasses 100 establish a wireless communication with a remote assistance device. At step 1426, the smart glasses 100 stream a live view video/image obtained by the camera to the remote assistance device. At step 1428, the smart glasses 100 receive notes transmitted from the remote assistance device. At step 1430, the smart glasses 100 present notes as an image overlay or picture-in-picture for displaying to the wearer of the smart glasses 100. At step 1432, the smart glasses 100 receive commands to further adjust camera settings during the wireless communication if necessary.

In one example scenario, a general dentist in a remote rural town comes across a patient with a unique case that he is not familiar with. The patient is in need of treatment urgently and cannot be rescheduled. With the VC/FP from the dentist wearing the smart glasses 100, the smart glasses 100 adjust and activate the camera(s) 302. The remote assistance could be another dentist with more experience in the procedure. Two dentists can connect with each other through the user device 416 associated with the experienced dentist and the smart glasses 100 worn by the treating dentist via the network 410. Using the VC/FP from the dentist, the smart glasses 100 may stream the dentist's live view video online to the remote assistance where the experienced dentist can offer guidance and/or instructions via voice communication to the treating dentist. The experienced dentist is also able to draw and annotate notes on the user device 416, and send the notes to the treating dentist. The smart glasses 100 worn by the treating dentist can then display the notes as an overlay in his field of view or as a picture-in-picture video on a corner of the projection that the dentist can quickly refer to.

In addition to providing any dentist with remote assistance whenever they encounter a problem, remote assistance with the operation of smart glasses is especially useful for a field medic on a battlefield. Usually a medic is trained to stabilize the wounded and to increase the chance of survival for injured soldiers. However, some injuries may require a much higher level of skill to stabilize the patient. The battlefield medic, with the smart glasses 100, can contact a remote assistance and connect with a military medical surgeon situated safely in a secure location. The surgeon can communicate with the field medic, write notes or sketch drawings to overlay on the medic's projection to better stabilize the wounded for transport.

Figure 14D:
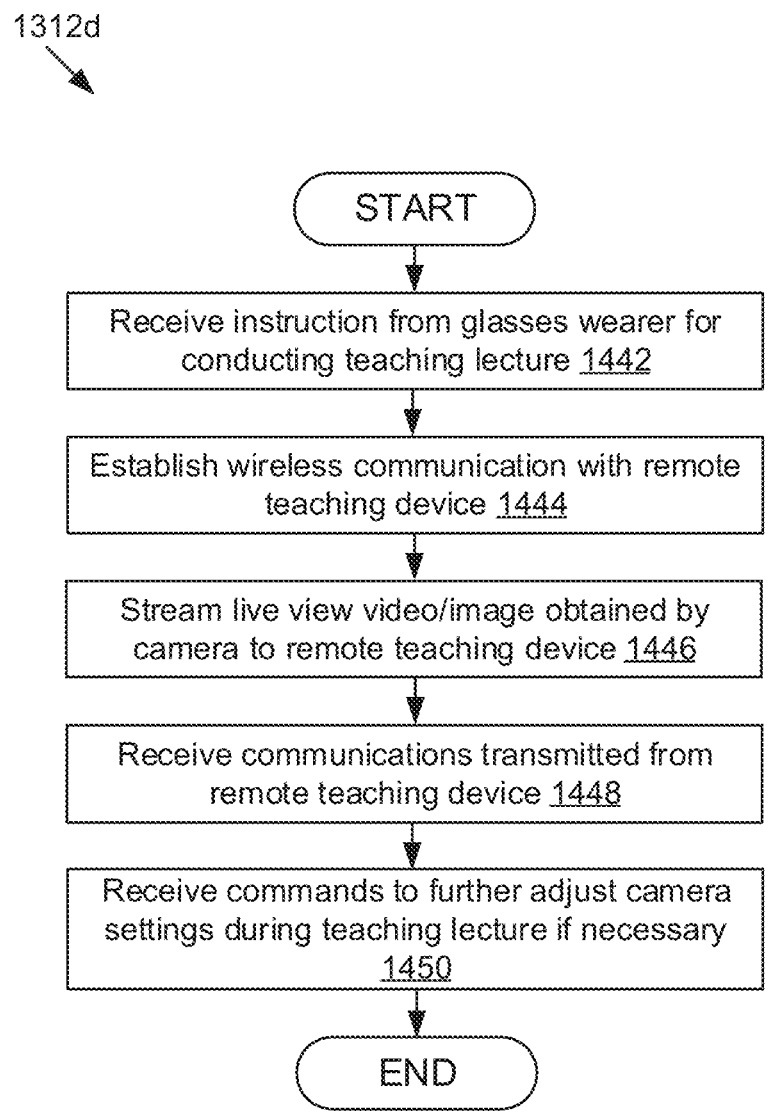

The flowchart 1312d of FIG. 14D illustrates a use case of a teaching scenario. According to the flowchart 1312d of FIG. 14D, at step 1442, the smart glasses 100 receive instruction from a glasses wearer for conducting a teaching course. At step 1444, the smart glasses 100 establish a wireless communication with a remote teaching device. At step 1446, the smart glasses 100 stream a live view video/image obtained by a camera to the remote teaching device. At step 1448, the smart glasses 100 receive communications transmitted from the remote teaching device. At step 1450, the smart glasses 100 receive commands to further adjust camera settings during the teaching lecture if necessary.

One scenario is a dental school where a professor has a unique case that he finds thinks would be a good example to teach his students. Another scenario is a continuing education scenario where fellow dentists meet in a continuing education seminar. In these scenarios, a dentist wearing the smart glasses 100 sends the VC/FP to activate the camera(s) 302 and a Wi☐Fi or cellular connection. The smart glasses 100 also stream the live view video feed to remote audiences (i.e., students and attendees). The audience can see exactly what the dentist sees in real☐time, for example, the verbal description of the dentist about the procedures and steps he is going to perform.

Additionally, the audience can also interact with the dentist via voice communication for questions and answers session. Suppose an attendee asks about a specific step. To answer the question, with the VC/FP from the dentist, the smart glasses 100 switch to a high magnification to explain and demonstrate how the procedure is performed. Once a satisfactory answer/explanation is given, the dentist's VC/FP allows the smart glasses 100 to switch back to a low magnification and resume the procedure. Upon receiving the VC/FP, the smart glasses 100 may also switch between the white LED lamp and the amber LED lamp as needed during the procedure to ensure a hands☐free operation. The smart glasses alone can be used to perform all the mentioned steps, and thus eliminating the need for a separate audio/video (A/V) equipment that would otherwise be needed to capture and broadcast the video feed.

In the above description, for purposes of explanation, numerous specific details are set forth in order to provide a thorough understanding of the present disclosure. However, it should be understood that the technology described herein can be practiced without these specific details. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

To ease description, some elements of the system and/or the methods are referred to using the labels first, second, third, etc. These labels are intended to help to distinguish the elements but do not necessarily imply any particular order or ranking unless indicated otherwise.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms including "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Various implementations described herein may relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of an entirely hardware implementation, an entirely software implementation, or implementations containing both hardware and software elements. For instance, the technology may be implemented in software, which includes but is not limited to firmware, resident software, microcode, etc. Furthermore, the technology can take the form of a computer program object accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input or I/O devices (including but not limited to keyboards, displays, pointing devices, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, Ethernet adapters, and Modems, are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), WebSocket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. As will be understood by those familiar with the art, the specification may be embodied in other specific forms without departing from the spirit or essential characteristics thereof. Likewise, the particular naming and division of the modules, routines, features, attributes, methodologies and other aspects are not mandatory or significant, and the mechanisms that implement the specification or its features may have different names, divisions and/or formats. Furthermore, the modules, routines, features, attributes, methodologies, and other aspects of the disclosure can be implemented as software, hardware, firmware, or any combination of the foregoing. Also, wherever a component, an example of which is a module, of the specification is implemented as software, the component can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment.

What is claimed is:

1. A computer-implemented method comprising:
   receiving, with smart glasses, a user-initiated request for a specific operation;
   activating, using the smart glasses, a camera with initial settings;
   receiving user information;
   determining whether there is a user-specific setting for a wearer of the smart glasses;
   responsive to determining there are no user-specific settings,
     setting the camera to default settings;
     collecting camera adjustments by the wearer during subsequent operations;
     determining the user-specific settings based on the collection of the camera adjustments; and
   setting the camera to the user-specific settings of the glasses wearer when receiving another user-initiated request from the wearer;
   capturing an image of a patient using the camera;
   generating a floating image through a micro-projector and a specifically-coated prism coupled to the camera;
   receiving a user input to adjust a camera setting to adjust the floating image; and
   dynamically controlling, using the smart glasses, the camera for the specific operation.

2. The method of claim 1, wherein generating the floating image through a micro-projector and a specifically-coated prism coupled to the camera further comprises:
   activating the camera to capture a live view of a portrait;
   transmitting the live view via two micro-projectors to allow the live view to be projected onto a pair of specifically-coated prisms integrated into lenses of the smart glasses; and
   controlling the prisms to reflect projections into pupils of a glasses wearer to allow the floating image to be presented to the wearer.

3. The method of claim 1, wherein receiving the user input to adjust the camera setting to adjust the floating image comprises:
   determining whether a command for lighting operation is received; and
   responsive to determining that the command for lighting operation is received, turning on a light that emits a proper color.

4. The method of claim 1, wherein receiving the user input to adjust the camera setting to adjust the floating image comprises:
   determining whether a command for a liquid crystal display (LCD) electronic shutter operation is received; and
   responsive to determining that the command for the liquid crystal display (LCD) electronic shutter operation is received, activating the LCD electronic shutter.

5. The method of claim 1, wherein receiving the user input to adjust the camera setting to adjust the floating image comprises:
   determining whether a command for magnification adjustment is received; and
   responsive to determining that the command for magnification adjustment is received, adjusting magnification of a camera view.

6. The method of claim 1, wherein receiving the user input to adjust the camera setting to adjust the floating image comprises:
   determining whether a command for view angle adjustment is received; and
   responsive to determining that the command for view angle adjustment is received, adjusting an angle of camera housing relative to a glasses frame.

7. The method of claim 1, wherein dynamically, using the smart glasses, controlling the camera for the specific operation comprises:
   receiving a portrait image of a patient;
   automatically identifying the patient based on facial recognition;
   retrieving medical information of the patient based on facial recognition;
   presenting the medical information on the smart glasses;
   generating and presenting medical alerts based on the medical information of the patient;
   receiving instructions via the smart glasses toward the specific operation;
   recording certain data during a specific operation process; and
   storing the recorded data in a patient profile.

8. The method of claim 1, further comprising:
   receiving an instruction from a glasses wearer for conducting patient communication;
   establishing a wireless connection with an adjacent display device;
   wirelessly transmitting a live video stream to a display device for patient view; and
   receiving commands to further adjust camera settings during the specific operation if necessary.

9. The method of claim 1, further comprising:
   receiving an instruction from a glasses wearer for conducting remote assistance;
   establishing a wireless communication with a remote assistance device;
   streaming a live view video obtained by the camera to the remote assistance device;
   receiving notes transmitted from the remote assistance device;
   presenting the notes as an image overlay or picture-in-picture for display on the smart glasses; and receiving commands to further adjust camera settings during the wireless communication if necessary.

10. The method of claim 1, further comprising:
receiving an instruction from a glasses wearer for conducting a teaching lecture;
establishing a wireless communication with a remote teaching device;
streaming a live view video obtained by the camera to the remote teaching device;
receiving communications transmitted from the remote teaching device; and
receiving commands to further adjust camera settings during the teaching lecture if necessary.

11. A pair of smart glasses comprising:
a camera for capturing one or more images and videos; and
a control unit configured to:
   receive a user-initiated request for a specific operation;
   activate the camera with initial settings;
   receive user information;
   determine whether there is a user-specific setting for a wearer of the smart glasses;
   responsive to determining there are no user-specific settings,
     set the camera to default settings;
     collect camera adjustments from the wearer of the smart glasses during subsequent operations;
     determine the user-specific settings based on the collection of the camera adjustments; and
     set the camera to the user-specific settings of the glasses wearer when receiving another user-initiated request from the wearer of the smart glasses;
   generate a floating image through a micro-projector and a specifically-coated prism coupled to the camera; and
   receive a user input to adjust a camera setting to adjust the floating image; and
   dynamically control the camera for the specific operation.

12. The smart glasses of claim 11, wherein to generate the floating image through a micro-projector and a specifically-coated prism coupled to the camera, the control unit is further configured to:
activate the camera to capture a live view of a portrait;
transmit the live view via two micro-projectors to allow the live view to be projected onto a pair of specifically-coated prisms integrated into lenses of the smart glasses; and
control the prisms to reflect projections into pupils of a glasses wearer to allow the floating image to be presented to the wearer of the smart glasses.

13. The smart glasses of claim 11, wherein to receive the user input to adjust the camera setting to adjust the floating image, the control unit is further configured to:
determine whether a command for lighting operation is received; and
responsive to determining that the command for lighting operation is received, turn on a light that emits a proper color.

14. The smart glasses of claim 11, wherein to receive the user input to adjust the camera setting to adjust the floating image, the control unit is further configured to:
determine whether a command for a liquid crystal display electronic shutter operation is received; and
responsive to determining that the command for the liquid crystal display (LCD) electronic shutter operation is received, activate the LCD electronic shutter.

15. The smart glasses of claim 11, wherein to receive the user input to adjust the camera setting to adjust the floating image, the control unit is further configured to:
determine whether a command for magnification adjustment is received; and
responsive to determining that the command for magnification adjustment is received, adjust magnification of a camera view.

16. The smart glasses of claim 11, wherein to receive the user input to adjust the camera setting to adjust the floating image, the control unit is further configured to:
determine whether a command for view angle adjustment is received; and
responsive to determining that the command for view angle adjustment is received, adjust an angle of camera housing relative to a glasses frame.

17. The smart glasses of claim 11, wherein to dynamically control the camera for the specific operation, the control unit is further configured to:
receive a portrait image of a patient;
automatically identify the patient based on facial recognition;
retrieve medical information of the patient based on facial recognition;
present the medical information on the smart glasses;
generate and presenting medical alerts based on the medical information of the patient;
receive instructions via the smart glasses toward the specific operation;
record certain data during a specific operation process; and
store the recorded data in a patient profile.

* * * * *